(12) United States Patent
Field et al.

(10) Patent No.: US 7,419,981 B2
(45) Date of Patent: Sep. 2, 2008

(54) SYNERGISTIC COMBINATIONS OF AN ALPHA-2-DELTA LIGAND AND A CGMP PHOSPHODIETERSE 5 INHIBITOR

(75) Inventors: Mark John Field, Kent (GB); Richard Griffith Williams, Kent (GB)

(73) Assignee: Pfizer Inc., New York, NY (US)

( * ) Notice: Subject to any disclaimer, the term of this patent is extended or adjusted under 35 U.S.C. 154(b) by 109 days.

(21) Appl. No.: 10/771,183

(22) Filed: Feb. 3, 2004

(65) Prior Publication Data

US 2004/0157847 A1    Aug. 12, 2004

Related U.S. Application Data

(63) Continuation-in-part of application No. 10/640,515, filed on Aug. 13, 2003, now abandoned.

(60) Provisional application No. 60/411,493, filed on Sep. 16, 2002.

(30) Foreign Application Priority Data

Aug. 15, 2002   (GB) ................................ 0219024.7

(51) Int. Cl.
| | |
|---|---|
| A61K 31/519 | (2006.01) |
| A61K 31/53 | (2006.01) |
| A61K 31/498 | (2006.01) |
| A61K 31/195 | (2006.01) |
| C07D 471/04 | (2006.01) |
| C07D 471/22 | (2006.01) |
| C07D 241/38 | (2006.01) |
| C07D 229/28 | (2006.01) |

(52) U.S. Cl. .................. 514/252.16; 514/561; 514/565; 544/256; 544/343; 544/220; 562/507; 562/512; 564/462; 564/463

(58) Field of Classification Search ............ 514/252.16, 514/252, 559, 561, 565
See application file for complete search history.

(56) References Cited

U.S. PATENT DOCUMENTS 4,024,175 A   5/1977  Satzinger et al.
6,500,954 B1 * 12/2002  Gouliaev et al. ............. 546/139
6,500,955 B1 * 12/2002  Chawla et al. ............... 546/168
6,500,972 B2 * 12/2002  Cheng et al. ................. 552/296
6,579,879 B2 *  6/2003  Mylari ................... 514/252.01
2004/0157847 A1 *  8/2004  Field et al. ................... 514/246

FOREIGN PATENT DOCUMENTS

| EP | 0934061 | 7/1997 |
|---|---|---|
| EP | 1129706 | 10/2000 |
| EP | 641330 | 10/2001 |
| WO | WO0126659 | 4/2001 |
| WO | WO0128978 | 4/2001 |
| WO | WO02085839 | 10/2002 |
| WO | WO03082807 | 10/2003 |

OTHER PUBLICATIONS

2006 Chemical Abstracts Service Catalog, published by Chemical Abstracts Service, p. 52.*
Avery's Drug Treatment: Principles and Practice of Clinical Pharmacology and Therapeutics, 3rd Edition, 1987, Edited by Trevor M. Speight, Chapter VIII, pp. 255-282.*
The Merck Manual of Diagnosis and Therapy, seventeenth edition, 1999, Published by Merck Research Laboratories, pp. 1371-1372.*
Jain N, et al, "Sildenafil-induced peripheral analgesia and activation of the nitric oxide-cyclic GMP pathway" Brian Research, 2001, pp. 170-178, vol. 909.
Asomoza-Espinosa R, et al, "Sildenafil increases diclofenac antinociception in the formalin test" Eur. J. Pharm., 2001, pp. 195-200, vol. 418.
Mixcoatl-Zecuatl T, et al, "Seldenafil produces antinociception and increases morphine anitnociception in the formalin test" Eur. J. Pharm., 2000, pp. 81-87 vol. 400.

* cited by examiner

*Primary Examiner*—Shaojia Anna Jiang
*Assistant Examiner*—Eric S Olson
(74) *Attorney, Agent, or Firm*—Gregg C. Benson; A. Dean Olson

(57) ABSTRACT

The instant invention relates to a combination of an alpha-2-delta ligand and a PDEV inhibitor for use in therapy, particularly in the treatment of pain, particularly neuropathic pain. Particularly preferred alpha-2-delta ligands are gabapentin and pregabalin. A particularly preferred PDEV inhibitors is sildenafil.

6 Claims, 4 Drawing Sheets

Figure 1:
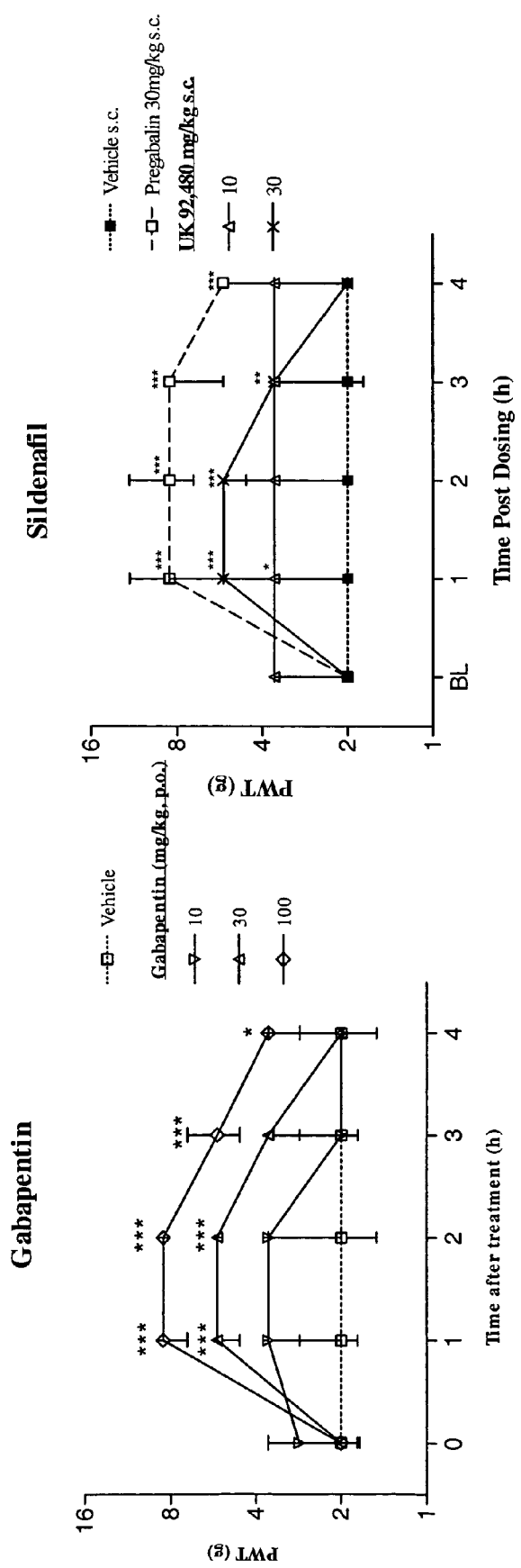

SYNERGISTIC COMBINATIONS OF AN ALPHA-2-DELTA LIGAND AND A CGMP PHOSPHODIETERSE 5 INHIBITOR

This application is a Continuation-In-Part application of U.S. Ser. No. 10/640515 filed Aug. 13, 2003 now abandoned, which claimed priority to U.S. Ser. No. 60/411,493 filed Sep. 16, 2002 and United Kingdom Application No. 0219024.7 filed Aug. 15, 2002.

FIELD OF THE INVENTION

This invention relates to combinations of an alpha-2-delta ligand and a cGMP PDEV ('PDEV') inhibitor, particularly those which exhibit a synergistic effect, particularly for the curative, prophylactic or palliative treatment of pain and related disorders.

BACKGROUND TO THE INVENTION

Alpha-2-delta ligands may be defined as compounds which selectively displace $^3$H-gabapentin from porcine brain membranes indicating a high affinity interaction with the alpha-2-delta ($\alpha_2\delta$) subunit of voltage-gated calcium channels. Alpha-2-delta ligands also includes compounds which do not displace $^3$H-gabapentin, but are structurally similar to compounds that do, which might be expected to bind alpha-2-delta at a slightly different site than $^3$H-gabapentin or may bind to human brain alpha-2-delta but not porcine alpha-2-delta. They may also be known as GABA analogs.

Alpha-2-delta ligands have been described for a number of indications. The best known alpha-2-delta ligand, gabapentin (NEURONTIN®), 1-(aminomethyl)-cyclohexylacetic acid, was first described in the patent literature in the patent family comprising U.S. Pat. No. 4,024,175. The compound is approved for the treatment of epilepsy and neuropathic pain.

A second alpha-2-delta ligand, pregabalin, (S)-(+)-4-amino-3-(2-methylpropyl)butanoic acid, is described in European patent application publication number EP641330 as an anti-convulsant treatment useful in the treatment of epilepsy and in EP0934061 for the treatment of pain.

Further WO0128978, describes a series of alpha-2-delta ligands, particularly (1α,3α,5α)(3-amino-methyl-bicyclo[3.2.0]hept-3-yl)-acetic acid, depicted below:

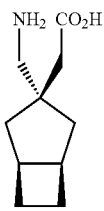

More recently, International Patent Application Number PCT/IB02/01146 (unpublished at the priority date of the present invention) and published as WO02/085839, describes a series of alpha-2-delta ligands of the following formulae:

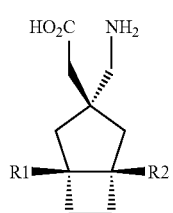 (I)

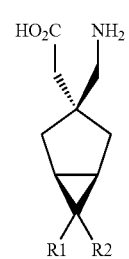 (II)

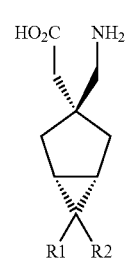 (III)

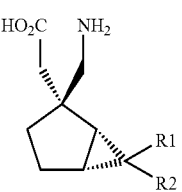 (IV)

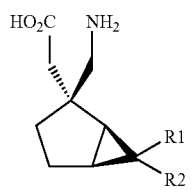 (V)

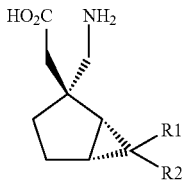 (VI)

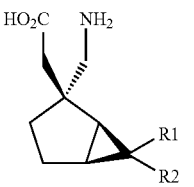 (VII)

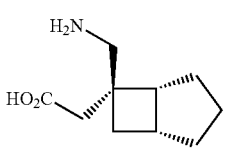 (VIII)

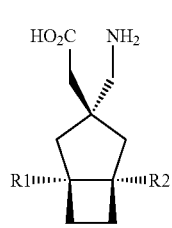 (IX)

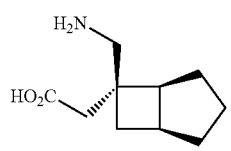
(X)
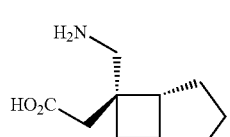
(XI)
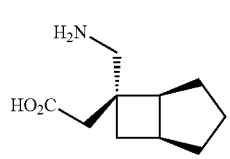
(XII)
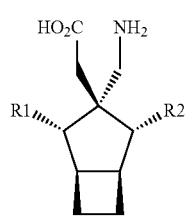
(XIII)
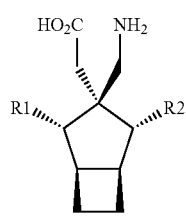
(XIV)
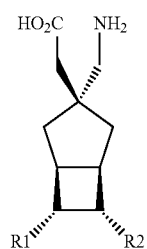
(XV)
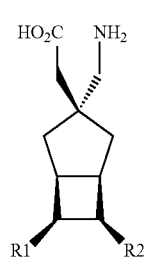
(XVI)
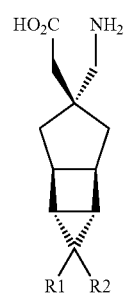
(XVII)
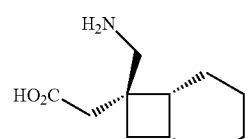
XVIII
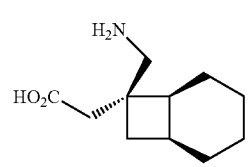
XIX
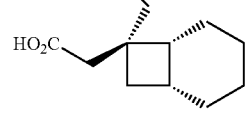
XX
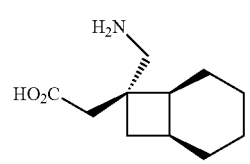
XXI
XXII
XXIII
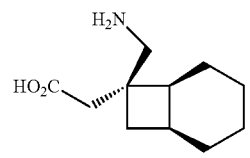
XXIV -continued

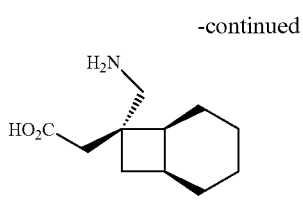

XXV wherein R[1] and R[2] are each independently selected from H, straight or branched alkyl of 1-6 carbon atoms, cycloalkyl of from 3-6 carbon atoms, phenyl and benzyl, subject to the proviso that, except in the case of a tricyclooctane compound of formula (XVII), R[1] and R[2] are not simultaneously hydrogen; for use in the treatment of a number of indications, including pain.

International Patent application No. PCT/IB03/00976, unpublished at the filing date of the present invention, describes compounds of the formula I, below:

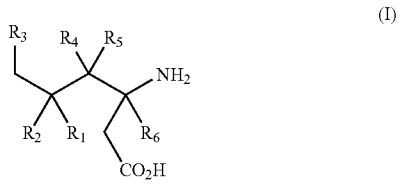

(I)

wherein $R_1$ is hydrogen or $(C_1-C_6)$alkyl optionally substituted with from one to five fluorine atoms;

$R_2$ is hydrogen or $(C_1-C_6)$alkyl optionally substituted with from one to five fluorine atoms; or $R_1$ and $R_2$, together with the carbon to which they are attached, form a three to six membered cycloalkyl ring;

$R_3$ is $(C_1-C_6)$alkyl, $(C_3-C_6)$cycloalkyl, $(C_3-C_6)$cycloalkyl-$(C_1-C_3)$alkyl, phenyl, phenyl-$(C_1-C_3)$alkyl, pyridyl, pyridyl-$(C_1-C_3)$alkyl, phenyl-N(H)—, or pyridyl-N(H)—, wherein each of the foregoing alkyl moieties can be optionally substituted with from one to five fluorine atoms, preferably with from zero to three fluorine atoms, and wherein said phenyl and said pyridyl and the phenyl and pyridyl moieties of said phenyl-$(C_1-C_3)$alkyl and said pyridyl-$(C_1-C_3)$alkyl, respectively, can be optionally substituted with from one to three substituents, preferably with from zero to two substituents, independently selected from chloro, fluoro, amino, nitro, cyano, $(C_1-C_3)$alkylamino, $(C_1-C_3)$alkyl optionally substituted with from one to three fluorine atoms and $(C_1-C_3)$ alkoxy optionally substituted with from one to three fluorine atoms;

$R_4$ is hydrogen or $(C_1-C_6)$alkyl optionally substituted with from one to five fluorine atoms;

$R_5$ is hydrogen or $(C_1-C_6)$alkyl optionally substituted with from one to five fluorine atoms; and $R_6$ is hydrogen or $(C_1-C_6)$alkyl;

and the pharmaceutically acceptable salts of such compounds.

Inhibitors of the cyclic guanosine 3',5'-monophosphate phosphodiesterase type five (cGMP PDEV) enzyme ('PDEV inhibitors') may be characterized by compounds with high affinity and selectivity for the PDEV enzyme with little or no affinity for the other phosphodiesterase isoforms and they have been described as being useful for treating a number of indications. In particular, sildenafil (5-[2-ethoxy-5-(4-methyl-1-piperazinylsulphonyl)phenyl]-1-methyl-3-n-propyl-1,6-dihydro-7H-pyrazolo[4,3-d]pyrimidin-7-one) (VIA-GRA®) has been described for the treatment of a number of cardiovascular disorders and has proved to be successful as the first orally effective treatment for male erectile dysfunction (MED). The use of PDEV inhibitors in the treatment of neuropathy has been described in European Patent Application Number EP1129706 and WO01/26659. Analgesic effects of sildenafil have recently been described in Jain et al, Brain Research, 909, 170-178 (2001); Asomoza-Espinosa et al, Eur. J. Pharm., 418, 195-200 (2001); and Mixcoatl-Zecutal et al, Eur. J. Pharm., 400, 81-87 (2001).

SUMMARY OF THE INVENTION

It has now been found that combination therapy with an alpha-2-delta ligand and a PDEV inhibitor results in unexpected improvement in the treatment of pain. When administered simultaneously, sequentially or separately, the alpha-2-delta ligand and PDEV inhibitor interact in a synergistic manner to control pain. This unexpected synergy allows a reduction in the dose required of each compound, leading to a reduction in the side effects and enhancement of the clinical effectiveness of the compounds and treatment.

Accordingly, as a first aspect, the invention provides a combination product comprising an alpha-2-delta ligand, excluding pregabalin and gabapentin, and a PDEV inhibitor. Alternatively, the exclusion may also include the compounds (i)-(xxv) of PCT/IB02/01146.

As an alternative or further aspect, the invention provides a synergistic combination product comprising an alpha-2-delta ligand and a PDEV inhibitor.

Examples of alpha-2-delta ligands for use with the present invention are those compounds generally or specifically disclosed in U.S. Pat. No. 4,024,175, particularly gabapentin, EP641330, particularly pregabalin, U.S. Pat. No. 5,563,175, WO9733858, WO9733859, WO9931057, WO9931074, WO9729101, WO02085839, particularly [(1R,5R,6S)-6-(Aminomethyl)bicyclo[3.2.0]hept-6-yl]acetic acid, WO9931075, particularly 3-(1-Aminomethyl-cyclohexylmethyl)-4H-[1,2,4]oxadiazol-5-one and C-[1-(1H-Tetrazol-5-ylmethyl)-cycloheptyl]-methylamine, WO9921824, particularly (3S,4S)-(1-Aminomethyl-3,4-dimethyl-cyclopentyl)-acetic acid, WO0190052, WO0128978, particularly (1α,3α,5α)(3-amino-methyl-bicyclo[3.2.0]hept-3-yl)-acetic acid, EP0641330, WO9817627, WO0076958, particularly (3S,5R)-3-aminomethyl-5-methyl-octanoic acid, PCT/IB03/00976, particularly (3S,5R)-3-amino-5-methyl-heptanoic acid, (3S,5R)-3-amino-5-methyl-nonanoic acid and (3S,5R)-3-Amino-5-methyl-octanoic acid, EP1178034, EP1201240, WO9931074, WO03000642, WO0222568, WO0230871, WO0230881, WO02100392, WO02100347, WO0242414, WO0232736, WO0228881, WO03080588, WO03065982, US20030181390, WO03077902, US20030176369, US20030171303, US20030083382, US20030236200, WO03104184, WO0309938, US20030216466, US20040006132 and WO 02100347, and pharmaceutically acceptable salts and solvates thereof, all of which are incorporated herein by reference.

Preferred alpha-2-delta ligands of the present invention include: gabapentin, pregabalin, [(1R,5R,6S)-6-(Aminomethyl)bicyclo[3.2.0]hept-6-yl]acetic acid, 3-(1-Aminomethyl-cyclohexylmethyl)-4H-[1,2,4]oxadiazol-5-one and C-[1-(1H-Tetrazol-5-ylmethyl)-cycloheptyl]-methylamine, (3S,4S)-(1-Aminomethyl-3,4-dimethyl-cyclopentyl)-acetic acid, (1α,3α,5α)(3-amino-methyl-bicyclo[3.2.0]hept-3-yl)-acetic acid, (3S,5R)-3-Aminomethyl-5-methyl-octanoic acid, (3S,5R)-3-amino-5-methyl-heptanoic acid, (3S,5R)-3-amino-5-methyl-nonanoic acid and (3S,5R)-3-Amino-5-methyl-octanoic acid.

Useful cyclic alpha-2-delta ligands of the present invention may be depicted by the following formula (I):

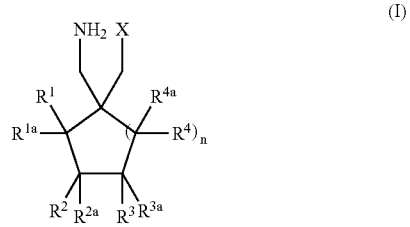

wherein X is a carboxylic acid or carboxylic acid bioisostere; n is 0, 1 or 2; and
$R^1$, $R^{1a}$, $R^2$, $R^{2a}$, $R^3$, $R^{3a}$, $R^4$ and $R^{4a}$ are independently selected from H and $C_1$-$C_6$ alkyl, or
$R^1$ and $R^2$ or $R^2$ and $R^3$ are taken together to form a $C_3$-$C_7$ cycloalkyl ring, which is optionally substituted with one or two substituents selected from $C_1$-$C_6$ alkyl, or a pharmaceutically acceptable salt or solvate thereof.

In formula (I), suitably, $R^1$, $R^{1a}$, $R^{2a}$, $R^{3a}$, $R^4$ and $R^{4a}$ are H and $R^2$ and $R^3$ are independently selected from H and methyl, or $R^{1a}$, $R^{2a}$, $R^{3a}$ and $R^{4a}$ are H and $R^1$ and $R^2$ or $R^2$ and $R^3$ are taken together to form a $C_3$-$C_7$ cycloalkyl ring, which is optionally substituted with one or two methyl substituents. A suitable carboxylic acid bioisostere is selected from tetrazolyl and oxadiazolonyl. X is preferably a carboxylic acid.

In formula (I), preferably, $R^1$, $R^{1a}$, $R^{2a}$, $R^{3a}$, $R^4$ and $R^{4a}$ are H and $R^2$ and $R^3$ are independently selected from H and methyl, or $R^{1a}$, $R^{2a}$, $R^{3a}$ and $R^{4a}$ are H and $R^1$ and $R^2$ or $R^2$ and $R^3$ are taken together to form a $C_4$-$C_5$ cycloalkyl ring, or, when n is 0, $R^1$, $R^{1a}$, $R^{2a}$, $R^{3a}$, $R^4$ and $R^{4a}$ are H and $R^2$ and $R^3$ form a cyclopentyl ring, or, when n is 1, $R^1$, $R^{1a}$, $R^{2a}$, $R^{3a}$, $R^4$ and $R^{4a}$ are H and $R^2$ and $R^3$ are both methyl or $R^1$, $R^{1a}$, $R^{2a}$, $R^{3a}$, $R^4$ and $R^{4a}$ are H and $R^2$ and $R^3$ form a cyclobutyl ring, or, when n is 2, $R^1$, $R^{1a}$, $R^2$, $R^{2a}$, $R^3$, $R^{3a}$, $R^4$ and $R^{4a}$ are H, or, n is 0, $R^1$, $R^{1a}$, $R^{2a}$, $R^{3a}$, $R^4$ and $R^{4a}$ are H and $R^2$ and $R^3$ form a cyclopentyl ring.

Useful acyclic alpha-2-delta ligands of the present invention may be depicted by the following formula (II):

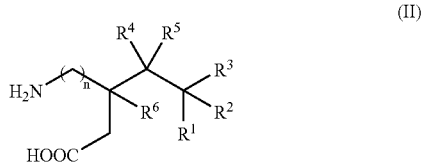

wherein:
n is 0 or 1, $R^1$ is hydrogen or ($C_1$-$C_6$)alkyl; $R^2$ is hydrogen or ($C_1$-$C_6$)alkyl; $R^3$ is hydrogen or ($C_1$-$C_6$)alkyl; $R^4$ is hydrogen or ($C_1$-$C_6$)alkyl; $R^5$ is hydrogen or ($C_1$-$C_6$)alkyl and $R^2$ is hydrogen or ($C_1$-$C_6$)alkyl, or a pharmaceutically acceptable salt or solvate thereof.

According to formula (II), suitably $R^1$ is $C_1$-$C_6$ alkyl, $R^2$ is methyl, $R^3$—$R^6$ are hydrogen and n is 0 or 1. More suitably $R^1$ is methyl, ethyl, n-propyl or n-butyl, $R^2$ is methyl, $R^3$-$R^6$ are hydrogen and n is 0 or 1. When $R^2$ is methyl, $R^3$-$R^6$ are hydrogen and n is 0, $R^1$ is suitably ethyl, n-propyl or n-butyl.

When $R^2$ is methyl, $R^3$—$R^6$ are hydrogen and n is 1, $R^1$ is suitably methyl or n-propyl. Compounds of formula (II) are suitably in the 3S,5R configuration.

Examples of PDEV inhibitors for use with the invention are: the pyrazolo [4,3-d]pyrimidin-7-ones disclosed in EP-A-0463756; the pyrazolo [4,3-d]pyrimidin-7-ones disclosed in EP-A-0526004; the pyrazolo [4,3-d]pyrimidin-7-ones disclosed in published international patent application WO 93/06104; the isomeric pyrazolo [3,4-d]pyrimidin-4-ones disclosed in published international patent application WO 93/07149; the quinazolin-4-ones disclosed in published international patent application WO 93/12095; the pyrido [3,2-d]pyrimidin-4-ones disclosed in published international patent application WO 94/05661; the purin-6-ones disclosed in published international patent application WO 94/00453; the pyrazolo [4,3-d]pyrimidin-7-ones disclosed in published international patent application WO 98/49166; the pyrazolo [4,3-d]pyrimidin-7-ones disclosed in published international patent application WO 99/54333; the pyrazolo [4,3-d]pyrimidin-4-ones disclosed in EP-A-0995751; the pyrazolo [4,3-d]pyrimidin-7-ones disclosed in published international patent application WO 00/24745; the pyrazolo [4,3-d]pyrimidin-4-ones disclosed in EP-A-0995750; the hexahydropyrazino [2',1':6,1]pyrido [3,4-b]indole-1,4-diones disclosed in published international application WO95/19978; the imidazo[5,1-f][1,2,4]triazin-ones disclosed in EP-A-1092719 and in published international application WO 99/24433; and the bicyclic compounds disclosed in published international application WO 93/07124; all of which are incorporated herein by reference.

Further examples of suitable PDEV inhibitors for use herein include: the pyrazolo [4,3-d]pyrimidin-7-ones disclosed in published international application WO 01/27112; the pyrazolo [4,3-d]pyrimidin-7-ones disclosed in published international application WO 01/27113; the compounds disclosed in EP-A-1092718 and the compounds disclosed in EP-A-1092719; the tricyclic compounds disclosed in EP-A-1241170; the alkyl sulphone compounds disclosed in published international application WO 02/074774; the compounds disclosed in published international application WO 02/072586; the compounds disclosed in published international application WO 02/079203; the compounds described in WO01187882; the compounds described in WO0056719, e.g. BMS-341400; the compounds described in WO9964004, e.g. BMS-263504; the compounds described in EP-1057829 (Jordanian Pharmaceutical Manufacturing and Medical Equipment Company); the compounds described in EP722936; the compounds described in WO93/07124; the compounds described in WO98/06722; the compounds described in WO98/06722; the compounds described in EP579496 and in particular ONO1505 (Ono); the compounds described in WO97/03070 and in particular OPC35564 (Otsuka); and the compounds described in WO 02/074312; all of which are incorporated herein by reference.

Yet further examples of suitable PDEV inhibitors for use herein include the carboline derivatives described in WO03000691, WO02098875, WO02064591, WO02064590 and WO0108688, the pyrazino [1',2':1,6]pyrido [3,4-B]indole 1,4-dione derivatives described in WO02098877, the tetracyclic compounds described in WO02098428, the compounds described in WO02088123 and WO0200656, the condensed pyrazindione derivatives described in WO0238563 and WO2000657, the indole derivatives described in WO0236593, the condensed pyrindole derivatives described in WO0228865 and WO0228859, the hexahydropyrazino[1',2':1,6]-pyrido [3,4-B]indole-1,4-dione derivatives described in WO0228858 and WO0194345, the fused heterocyclic derivatives described in WO0210166, the cyclic GMP specific phosphodiesterase inhibitors described in WO0200658, the tetracyclic diketopiperazine compounds described in WO0194347, the compounds described in WO0298877 and the compounds described in use application WO0219213, all of which are incorporated herein by reference.

Yet further examples of suitable PDEV inhibitors for use herein include the compounds described in WO0164192, DE 10104800, WO0259126, DE 10104095, WO0249651, DE10063224, DE10060338, DE10058662 and WO0200660, all of which are incorporated herein by reference.

Still other PDEV inhibitors inhibitors useful in conjunction with the present invention include: 4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)arnino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); ER-118585, E-8010, E-4021 and E-4010 (Eisai); Bay-38-3045 & 38-9456 (Bayer); FR181074, FR229934 and FR226807 (Fujisawa); TA-1032, T-0156 and TA-1790 (Tanabe Seiyaku); EMD82639 and EMR6203 (Merck); LAS34179 and LAS35917 (Almirall); Sch-51866; BMS-223131 (Bristol Myers Squibb); NCX911 (Nicox); and ABT-724 and ABT-670 (Abbott).

Preferred PDEV inhibitors for the use according to the present invention include:

(i) 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756);

(ii) 5-(2-ethoxy-5-morpholinoacetylphenyl)-1-methyl-3-n-propyl-1,6-dihydro-7H-pyrazolo[4,3-d]pyrimidin-7-one (see EP-A-0526004);

(iii) 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166);

(iv) 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333);

(v) (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333);

(vi) 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8);

(vii) 5-[2-iso-Butoxy-5-(4-ethylpiperazin-1-ylsulphonyl) pyridin-3-yl]-3-ethyl-2-(1-methylpiperidin-4-yl)-2,6-dihydro-7H-pyrazolo[4,3-d]pyrimidin-7-one
(see WO 01/27113, Example 15);

(viii) 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66);

(ix) 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124);

(x) 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132);

(xi) (6R,12aR)-2,3,6,7,12,12a-hexahydro-2-methyl-6-(3,4-methylenedioxyphenyl)-pyrazino[2',1':6,1]pyrido[3,4-b]indole-1,4-dione (tadalafil, IC-351, Cialis®), i.e. the compound of examples 78 and 95 of published international application WO95/19978, as well as the compound of examples 1, 3, 7 and 8;

(xii) 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433;

(xiii) the pyrazolo [4,3-d]pyrimidin-4-ones disclosed in WO00/27848, in particular N-[[3-(4,7-dihydro-1-methyl-7-oxo-3-propyl-1H-pyrazolo[4,3-d]-pyrimidin-5-yl)-4-propxyphenyl]sulfonyl]-1-methyl2-pyrrolidinepropanamide [DA-8159 (Example 68 of WO00/27848)];

(xiv) the compound of example 11 of published international application WO93/07124;

(xv) 4-(4-chlorobenzyl)amino-6,7,8-trimethoxyquinazoline; and (xvi) 7,8-dihydro-8-oxo-6-[2-propoxyphenyl]-1H-imidazo[4,5-g]quinazoline;

(xvii) 1-[3-[1-[(4-fluorophenyl)methyl]-7,8-dihydro-8-oxo-1H-imidazo[4,5-g]quinazolin-6-yl]-4-propoxyphenyl]carboxamide;

(xviii) 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one; and (xix) 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine; and pharmaceutically acceptable salts and solvates thereof.

The suitability of any particular PDEV inhibitor can be readily determined by evaluation of its potency and selectivity using literature methods followed by evaluation of its toxicity, absorption, metabolism, pharmacokinetics, etc in accordance with standard pharmaceutical practice.

Preferably, the PDEV inhibitors have an $IC_{50}$ at less than 100 nanomolar, more preferably, at less than 50 nanomolar, more preferably still at less than 10 nanomolar.

IC50 values for the PDEV inhibitors may be determined using the PDE5 assay described hereinafter.

Preferably the PDEV inhibitors used in the pharmaceutical combinations according to the present invention are selective for the PDEV enzyme. Preferably they have a selectivity of PDEV over PDE3 of greater than 100 more preferably greater than 300. More preferably the PDEV inhibitor has a selectivity over both PDE3 and PDE4 of greater than 100, more preferably greater than 300. Selectivity ratios may readily be determined by the skilled person. IC50 values for the PDE3 and PDE4 enzyme may be determined using established literature methodology, see S A Ballard et al, Journal of Urology, 1998, vol. 159, pages 2164-2171 and as detailed herein after.

Useful PDEV inhibitors of the present invention may be depicted by the following formula (III):

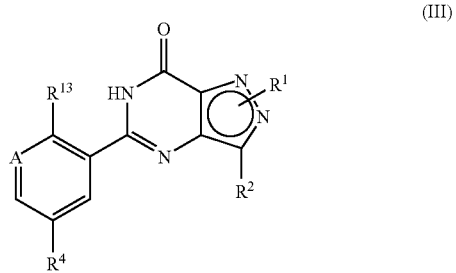

(III)

wherein:

A is CH or N;

$R^1$ is H, $C_1$ to $C_6$ alkyl, $C_3$ to $C_6$ alkenyl, $C_3$ to $C_6$ cycloalkyl, $C_3$ to $C_6$ cycloalkenyl, or $C_1$-$C_3$ perfluoroalkyl, wherein said alkyl group may be branched or straight chain and wherein said alkyl, alkenyl, cycloalkyl or perfluoroalkyl group is optionally substituted by; one or more substituents selected from: hydroxy; $C_1$ to $C_4$ alkoxy; $C_3$ to $C_6$ cycloalkyl; $C_1$-$C_3$ perfluoroalkyl; phenyl substituted with one or more substitutents selected from $C_1$ to $C_3$ alkyl, $C_1$ to $C_4$ alkoxy, $C_1$ to $C_4$ haloalkyl or $C_1$ to $C_4$ haloalkoxy wherein said haloalkyl and haloalkoxy groups contain one or more halo atoms, halo, CN, $NO_2$, $NHR^{11}$, $NHSO_2R^{12}$, $SO_2R^{12}$, $SO_2NHR^{11}$, $COR^{11}$, $CO_2R^{11}$ wherein $R^{11}$ is H, $C_1$ to $C_4$ alkyl, $C_2$ to $C_4$ alkenyl, $C_1$ to $C_4$ alkanoyl, $C_1$ to $C_4$ haloalkyl or $C_1$ to $C_4$ haloalkoxy and wherein $R^{12}$ is $C_1$ to $C_4$ alkyl, $C_2$ to $C_4$ alkenyl, $C_1$ to $C_4$ alkanoyl, $C_1$ to $C_4$ haloalkyl or $C_1$ to $C_4$ haloalkoxy; $NR^7R^8$, $CONR^7R^8$ or $NR^7COR^{11}$ wherein $R^7$ and $R^8$ are each independently selected from H, $C_1$ to $C_4$ alkyl, $C_2$ to $C_4$ alkenyl, $C_1$ to $C_4$ alkoxy, $CO_2R^9$, $SO_2R^9$ wherein said alkyl, alkenyl or alkoxy groups are optionally substituted by $NR^5R^6$, $C_1$ to $C_4$ haloalkyl or $C_1$ to $C_4$ haloalkoxy and wherein $R^9$ is H, hydroxy $C_2$ to $C_3$ alkyl, $C_1$, to $C_4$ alkanoyl or $C_1$, to $C_4$ alkyl which is optionally substituted with phenyl wherein said phenyl group is optionally substituted by one or more substituents selected from $C_1$ to $C_4$ alkyl optionally substituted by $C_1$ to $C_4$ haloalkyl or $C_1$ to $C_4$ haloalkoxy, $C_1$ to $C_4$ alkoxy, halo, CN, $NO_2$, $NHR^{11}$, $NHSO_2R^{12}$, $SO_2R^{12}$, $SO_2NHR^{11}$, $COR^{11}$ or $CO_2R^{11}$; $Het^1$; $Het^2$ or $Het^3$; or $R^1$ is $Het^4$ or phenyl wherein said phenyl group is optionally substituted by one or more substituents selected from $C_1$ to $C_4$ alkyl, $C_2$ to $C_4$ alkenyl, $C_1$ to $C_4$ alkoxy, halo, CN, $CF_3$, $OCF_3$, $NO_2$, $NHR^{11}$, $NHSO_2R^{12}$, $SO_2R^{12}$, $SO_2NHR^{11}$, $COR^{11}$, $CO_2R^{11}$;

$R^2$ is H, $C_1$ to $C_6$ alkyl, $C_3$ to $C_6$ alkenyl or $(CH_2)_n(C_3$ to $C_6$ cycloalkyl) wherein n is 0, 1 or 2 and wherein said alkyl or alkyenyl group is optionally substituted with one or more fluoro substituents;

$R^{13}$ is $OR^3$ or $NR^5R^6$;

$R^3$ is $C_1$ to $C_6$ alkyl, $C_3$-$C_6$ alkenyl, $C_3$-$C_6$ alkynyl, $C_3$-$C_7$ cycloalkyl, $C_1$-$C_6$ perfluoroalkyl or $(C_3$-$C_6$ cycloalkyl)$C_1$-$C_6$ alkyl optionally substituted with one or two substituents selected from $C_3$ to $C_5$ cycloalkyl, hydroxy, $C_1$ to $C_4$ alkoxy, $C_3$-$C_6$ alkenyl, $C_3$-$C_6$ alkynyl, benzyloxy, $NR^5R^6$, phenyl, $Het^1$, $Het^2$, $Het^3$ or $Het^4$ wherein the $C_1$ to $C_6$ alkyl and $C_1$ to $C_4$ alkoxy groups may optionally be terminated by a haloalkyl group such as $CF_3$; $C_3$ to $C_6$ cycloalkyl; $Het^1$, $Het^2$, $Het^3$ or $Het^4$;

$R^4$ is $C_1$-$C_4$ alkyl optionally substituted with OH, $NR^5R^6$, CN, $CONR^5R^6$ or $CO_2R^7$; $C_2$-$C_4$ alkenyl optionally substituted with CN, $CONR^5R^6$ or $CO_2R^7$; $C_2$-$C_4$ alkanoyl optionally substituted with $NR^5R^6$; hydroxy $C_2$-$C_4$ alkyl optionally substituted with $NR^5R^6$; $(C_2$-$C_3$ alkoxy)$C_1$-$C_2$ alkyl optionally substituted with OH or $NR^5R^6$; $CONR^5R^6$; $CO_2R^7$; halo; $NR^5R^6$; $NHSO_2NR^5R^6$; $NHSO_2R^8$; or phenyl or heterocyclyl either of which is optionally substituted with methyl; or $R^4$ is a pyrrolidinylsulphonyl, piperidinosulphonyl, morpholinosulphonyl, or piperazin-1-ylsulphonyl group having a substituent, $R^{10}$ at the 4-position of the piperazinyl group wherein said piperazinyl group is optionally substituted with one or two $C_1$ to $C_4$ alkyl, $C_1$ to $C_3$ alkoxy, $NR^7R^8$ or $CONR^7R^8$ groups and is optionally in the form of its 4-N-oxide;

$R^5$ and $R^6$ are each independently selected from H and $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl, morpholinyl, 4-($NR^9$)-piperazinyl or imidazolyl group wherein said group is optionally substituted with methyl or hydroxy;

$R^{10}$ is H; $C_1$ to $C_6$ alkyl, $(C_1$-$C_3$ alkoxy) $C_2$-$C_6$ alkyl, hydroxy $C_2$-$C_6$ alkyl, $(R^7R^8N)C_2$-$C_6$ alkyl, $(R^7R^8NCO)C_1$-$C_6$ alkyl, $CONR^7R^8$, $CSNR^7R^8$ or $C(NH)NR^7R^8$ optionally substituted with one or two substituents selected from hydroxy, $NR^5R^6$, $CONR^5R^6$, phenyl optionally substituted with $C_1$ to $C_4$ alkyl or $C_1$ to $C_4$ alkoxy; $C_2$ to $C_6$ alkenyl or $Het^4$;

$Het^1$ is an N-linked 4-, 5- or 6-membered nitrogen-containing heterocyclic group optionally containing one or more further heteroatoms selected from S, N or O;

$Het^2$ is a C-linked 5-membered heterocyclic group containing an O, S or N heteroatom optionally containing one or more heteroatoms selected from O or S;

$Het^3$ is a C-linked 6-membered heterocyclic group containing an O or S heteroatom optionally containing one or more heteroatoms selected from O, S or N or $Het^3$ is a C-linked 6-membered heterocyclic group containing three N heteroatoms;

$Het^4$ is a C-linked 4-, 5- or 6-membered heterocyclic group containing one, two or three heteroatoms selected from S, O or N; and wherein any of said heterocyclic groups $Het^1$, $Het^2$, $Het^3$ or $Het^4$ may be saturated, partially unsaturated or aromatic and wherein any of said heterocyclic groups may be optionally substituted with one or more substituents selected from $C_1$ to $C_4$ alkyl, $C_2$ to $C_4$ alkenyl, $C_1$ to $C_4$ alkoxy, halo, $CO_2R^{11}$, $COR^{11}$, $SO_2R^{12}$ or $NHR^{11}$ and/or wherein any of said heterocyclic groups is benzo-fused;

or wherein when $R^{13}$ represents $OR^3$ or $R^3NR^5$; $R^1$ represents Het, alkylHet, aryl or alkylaryl, which latter five groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$; $R^2$ represents H, halo, cyano, nitro, $OR^6$, $OC(O)R^7$, $C(O)R^8$, $C(O)OR^9$, $C(O)NR^{10}R^{11}$, $NR^{12}R^{13}$, $SO_2NR^{14}R^{15}$, lower alkyl, Het, alkyl-Het, aryl or alkylaryl, which latter five groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$; $R^3$ represents H, lower alkyl, alkylHet or alkylaryl, which latter three groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$; $R^4$ represents H, halo, cyano, nitro, halo(loweralkyl), $OR^6$, $OC(O)R^7$, $C(O)R^8$, $C(O)OR^9$, $C(O)NR^{10}R^{11}$, $NR^{12}R^{13}$, $NR^{16}Y(O)R^{17}$, $SOR^{18}$, $SO_2R^{19}R^{20}$, C(O)AZ, lower alkyl, lower alkenyl, lower alkynyl, Het, alkylHet, aryl, alkylaryl, which latter seven groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$; Y represents C or S(O), wherein one of $R^{16}$ and $R^{17}$ is not present when Y is S(O); A represents lower alkylene; Z represents $OR^6$, halo, Het or aryl, which latter two groups are both optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}OR^{11}$, $NR^{12}R^{13}$ and $SO_2NR^{14}R^{15}$; $R^5$, $R^6$, $R^7$, $R^8$, $R^9$, $R^{18}$, $R^{19}$ and $R^{20}$ independently represent H or lower alkyl; $R^{10}$ and $R^{11}$ independently represent H or lower alkyl, which latter group is optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$ or Het or aryl optionally substituted with one or more of said latter eleven groups or one of $R^{10}$ and $R_{11}$ may be lower alkoxy, amino or Het, which latter two groups are both optionally substituted with lower alkyl; $R^{12}$ and $R^{13}$ independently represent H or lower alkyl or one of $R^{12}$ or $R^{13}$ may be C(O)-lower alkyl or C(O)Het in which Het is optionally substituted with lower alkyl; $R^{14}$ and $R^{15}$ independently represent H or lower alkyl or $R^{14}$ and $R^{15}$ together with the nitrogen atom to which they are bound, form a heterocyclic ring; $R^{16}$ and $R^{17}$ independently represent H or lower alkyl or one of $R^{16}$ and $R^{17}$ may be Het or aryl, which latter two groups are both optionally substituted with lower alkyl; Het represents an optionally substituted four to twelve membered heterocyclic group, which may be aromatic or non-aromatic, which may contain one or more double bonds, which may be mono- or bi-cyclic and which contains one or more heteroatoms selected from N, S and O; or a pharmaceutically acceptable salt or solvate of any thereof.

In formula (III), the PDEV inhibitor may contain halo groups. Here, "halo" means fluoro, chloro, bromo or iodo.

In formula (III), the PDE5 inhibitor may contain one or more of alkyl, alkoxy, alkenyl, alkylene and alkenylene groups—which may be unbranched- or branched-chain.

In formula (III), a preferred group of compounds for use according to the present invention are those wherein: $R^1$ is H, methyl or ethyl; $R^2$ is H, $C_1$-$C_3$ alkyl optionally substituted by OH, or methoxy; $R^3$ is $C_2$-$C_3$ alkyl or allyl; $R^4$ is a sulphonylpiperidino or 4-N-($R^{10}$)-sulphonylpiperazin-1-yl group; $R^5$ is H, $NR^7R^8$, or $CONR^7R^8$; $R^{10}$ is H, $C_1$-$C_3$ alkyl, hydroxy $C_2$-$C_6$ alkyl, $CONR^7R^8$, $CSNR^7R^8$ or $C(NH)NR^7R^8$; $R^7$ and $R^8$ are each independently H or methyl.

In formula (III), another preferred group of compounds for use according to the present invention are those wherein: $R^1$ is $C_1$ to $C_2$ alkyl optionally substituted with Het; 2-(morpholin-4-yl)ethyl or benzyl; $R^2$ is $C_2$ to $C_4$ alkyl; $R^{13}$ is $OR^3$ or $NR^5R^6$; $R^3$ is $C_1$ to $C_4$ alkyl optionally substituted with one or two substituents selected from cyclopropyl, cyclobutyl, OH, methoxy, ethoxy, benzyloxy, $NR^5R^6$, phenyl, furan-3-yl, pyridin-2-yl and pyridin-3-yl; cyclobutyl; 1-methylpiperidin-4-yl; tetrahydrofuran-3-yl or tetrahydropyran-4-yl; $R^5$ and $R^6$ are each independently selected from H and $C_1$ to $C_2$ alkyl optionally substituted with cyclopropyl or methoxy, or, together with the nitrogen atom to which they are attached, form a azetidinyl, pyrrolidinyl or morpholinyl group; $R^7$ and $R^8$ together with the nitrogen atom to which they are attached, form a 4-$R^{10}$-piperazinyl group optionally substituted with one or two methyl groups and optionally in the form of its 4-N-oxide; $R^{10}$ is H, $C_1$ to $C_3$ alkyl optionally substituted with one or two substituents selected from OH, $NR^5R^6$, $CONR^5R^6$, phenyl optionally substituted with methoxy, benzodioxol-5-yl and benzodioxan-2-yl; allyl; pyridin-2-yl; pyridin-4-yl or pyrimidin-2-yl; and Het is selected from pyridin-2-yl; 1-oxidopyridin-2-yl; 6-methylpyridin-2-yl; 6-methoxypyridin-2-yl; pyridazin-3-yl; pyrimidin-2-yl and 1-methylimidazol-2-yl. Of this group more preferred are those compounds wherein $R^1$ is $C_1$ to $C_2$ alkyl optionally substituted with Het; 2-(morpholin-4-yl)ethyl or benzyl; $R^2$ is $C_2$ to $C_4$ alkyl; $R^{13}$ is $OR^3$; $R^3$ is $C_1$ to $C_4$ alkyl optionally monosubstituted with cyclopropyl, cyclobutyl, OH, methoxy, ethoxy, phenyl, furan-3-yl or pyridin-2-yl; cyclobutyl; tetrahydrofuran-3-yl or tetrahydropyran-4-yl; $R^7$ and $R^8$ together with the nitrogen atom to which they are attached, form a 4-$R^{10}$-piperazinyl group optionally in the form of its 4-N-oxide; $R^{10}$ is $C_1$ to $C_3$ alkyl optionally monosubstituted with OH; and Het is selected from pyridin-2-yl; 1-oxidopyridin-2-yl; 6-methylpyridin-2-yl; 6-methoxypyridin-2-yl; pyridazin-3-yl; pyrimidin-2-yl and 1-methylimidazol-2-yl.

In formula (III), one other further preferred group of compounds for use according to the present invention are those wherein: $R^1$ is $C_1$ to $C_6$ alkyl or $C_3$ to $C_6$ alkenyl wherein said alkyl or alkenyl groups may be branched chain or straight chain or $R^1$ is $C_3$ to $C_6$ cycloalkyl or $C_4$ to $C_6$ cycloalkenyl and wherein when $R^1$ is $C_1$ to $C_3$ alkyl said alkyl group is substituted by; and wherein when $R^1$ is $C_4$ to $C_6$ alkyl, $C_3$ to $C_6$ alkenyl, $C_3$ to $C_6$ cycloalkyl or $C_4$ to $C_6$ cycloalkenyl said alkyl, alkenyl, cycloalkyl or cycloalkenyl group is optionally substituted by; one or more substituents selected from: hydroxy; $C_1$ to $C_4$ alkoxy; $C_3$ to $C_4$ cycloalkyl; phenyl substituted with one or more substitutents selected from $C_1$ to $C_3$ alkyl, $C_1$ to $C_4$ alkoxy, $C_1$ to $C_4$ haloalkyl or $C_1$ to $C_4$ haloalkoxy, halo, CN, $NO_2$, $NHR^{11}$, $NHCOR^{12}$, $NHSO_2R^{12}$, $SO_2R^{12}$, $SO_2NHR^{11}$, $COR^{11}$, $CO_2R^{11}$ wherein said haloalkyl and haloalkoxy groups contain one or more halo atoms; $NR^7R^8$, $CONR^7R^8$ or $NR^7COR^{11}$; a $Het^1$ group which is an N-linked 4-membered N-containing heterocyclic group; a $Het^2$ group which is a C-linked 5-membered heterocyclic group containing an O, S or N heteroatom optionally containing one or more heteroatoms selected from N, O or S; a $Het^3$ group which is a C-linked 6-membered heterocyclic group containing an O or S heteroatom optionally containing one or more heteroatoms selected from O, S or N or a $Het^3$ group which is a C-linked 6-membered heterocyclic group containing three N heteroatoms; wherein $R^7$, $R^8$, $R^{11}$ and $R^{12}$ are as previously defined herein or $R^1$ is a $Het^4$ group which is a C-linked 4- or 5-membered heterocyclic group containing one heteroatom selected from S, O or N; a $Het^4$ group which is a C-linked 6-membered heterocyclic group containing one, two or three heteroatoms selected from S or O; a $Het^4$ group which is a C-linked 6-membered heterocyclic group containing three nitrogen heteroatoms; a $Het^4$ group which is a C-linked 6-membered heterocyclic group containing one or two nitrogen heteroatoms which is substituted by one or more substitutents selected from $C_1$ to $C_4$ alkyl, $C_1$ to $C_4$ alkoxy, $CO_2R^{11}$, $SO_2R^{12}$, $COR^{11}$, $NHR^{11}$ or $NHCOR^{12}$ and optionally including a further heteroatom selected from S, O or N wherein any of said heterocyclic groups $Het^1$, $Het^2$, $Het^3$ or $Het^4$ is saturated, partially unsaturated or aromatic as appropriate and wherein any of said heterocyclic groups is optionally substituted with one or more substituents selected from $C_1$ to $C_4$ alkyl, $C_3$ to $C_4$ alkenyl, $C_1$ to $C_4$ alkoxy, halo, $CO_2R^{11}$, $SO_2R^{12}$, $COR^{11}$ or $NHR^{11}$ wherein $R^{11}$ is as defined hereinbefore and/or wherein any of said heterocyclic groups is benzo-fused; or $R^1$ is phenyl substituted by one or more substituents selected from $CF_3$, $OCF_3$, $SO_2R^{12}$ or $CO_2R^{12}$ wherein $R^{12}$ is $C_1$ to $C_4$ alkyl which is optionally substituted by phenyl, $C_1$ to $C_4$ haloalkyl or $C_1$ to $C_4$ haloalkoxy wherein said haloalkyl and haloalkoxy groups contain one or more halo atoms; $R^2$ is $C_1$ to $C_6$ alkyl; $R^{13}$ is $OR^3$; $R^3$ is $C_1$ to $C_6$ alkyl optionally substituted with one or two substituents selected from $C_3$ to $C_5$ cycloalkyl, hydroxy, $C_1$ to $C_4$ alkoxy, benzyloxy, $NR^5R^6$, phenyl, furanyl, tetrahydrofuranyl or pyridinyl wherein said $C_1$ to $C_6$ alkyl and $C_1$ to $C_4$ alkoxy groups may optionally be terminated by a haloalkyl group such as $CF_3$; or $R^3$ is $C_3$ to $C_6$ cycloalkyl, 1-($C_1$ to $C_4$ alkyl) piperidinyl, tetrahydrofuranyl or tetrahydropyranyl; $R^4$ is a piperazin-1-ylsulphonyl group having a substituent $R^{10}$ at the 4-position of the piperazinyl group wherein said piperazinyl group is optionally substituted with one or two $C_1$ to $C_4$ alkyl groups and is optionally in the form of its 4-N-oxide; $R^5$ and $R^6$ are each independently selected from H and $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl or morpholinyl group; and $R^{10}$ is H; $C_1$ to $C_4$ alkyl optionally substituted with one or two substituents selected from hydroxy, $NR^5R^6$, $CONR^5R^6$, phenyl optionally substituted with $C_1$ to $C_4$ alkyl or $C_1$ to $C_4$ alkoxy; $C_3$ to $C_6$ alkenyl; $Het^4$; with the proviso that when $R^1$ is $C_1$ to $C_3$ alkyl substituted by phenyl then said phenyl group is not substituted by $C_1$ to $C_4$ alkoxy; CN; halo; $CF_3$; $OCF_3$; or $C_1$ to $C_4$ alkyl. More preferred of this group of compounds are those wherein $R^1$ is $C_1$ to $C_6$ alkyl wherein said alkyl may be branched or straight chain or $R^1$ is $C_3$ to $C_6$ cycloalkyl and wherein when $R^1$ is $C_1$ to $C_3$ alkyl said alkyl group is substituted by; and wherein when $R^1$ is $C_4$ to $C_6$ alkyl or $C_3$ to $C_6$ cycloalkyl said alkyl or cycloalkyl group is optionally substituted by; one or more substituents selected from: hydroxy; $C_1$ to $C_2$ alkoxy; $C_3$ to $C_5$ cycloalkyl; $NR^7R^8$, $NR^7COR^{11}$ or $COR^{11}$ wherein $R^7$ and $R^8$ are each independently selected from H, $C_1$ to $C_4$ alkyl or $CO_2R^9$ wherein $R^9$ and $R^{11}$ are as previously defined herein; a $Het^1$ group which is an N-linked 4-membered N-containing heterocyclic group; a $Het^3$ group which is a C-linked 6-membered heterocyclic group containing an O or S heteroatom optionally containing one or more heteroatoms selected from O, S or N or a $Het^3$ group which is a C-linked 6-membered heterocyclic group containing three N heteroatoms; or $R^1$ is a $Het^4$ group which is a C-linked 4-membered heterocyclic group containing one heteroatom selected from S, O or N or $R^1$ is a $Het^4$ group which is a C-linked 6-membered heterocyclic group containing one, two or three heteroatoms selected from S or O wherein any of said heterocyclic groups $Het^1$, $Het^2$, $Het^3$ or $Het^4$ is saturated, partially unsaturated or aromatic and is optionally substituted with one or more substituents selected from $C_1$ to $C_4$ alkyl, $C_1$ to $C_4$ alkoxy, $-CO_2R^{11}$, $-SO_2R^{12}$, $-COR^{11}$ or $NHR^{11}$ wherein $R^{11}$ and $R^{12}$ are as defined hereinbefore and/or wherein any of said heterocyclic groups is benzo-fused; or $R^1$ is phenyl substituted by one or more substituents selected from: $CF_3$, $-OCF_3$, $-SO_2R^{12}$, $-COR^{11}$, $-CO_2R^{11}$ wherein $R^{11}$ and $R^{12}$ are as defined hereinbefore; $R^2$ is $C_1$ to $C_6$ alkyl; $R^{13}$ is $OR^3$; $R^3$ is methyl, ethyl, n-propyl, i-propyl, n-butyl, sec-butyl, i-butyl or t-butyl alkyl optionally substituted with one or two substituents selected from cyclopropyl, cyclobutyl, hydroxy, methoxy, ethoxy, benzyloxy, phenyl, benzyl, furan-3-yl, tetrahydrofuran-2-ylmethyl, tetrahydrofuran-3-ylmethyl, pyridin-2-yl, pyridin-3-yl or $NR^5R^6$ wherein $R^5$ and $R^6$ are each independently selected from H and $C_1$ to $C_2$ alkyl; $R^4$ is a piperazin-1-ylsulphonyl group having a substituent, $R^{10}$ at the 4-position of the piperazinyl group wherein said piperazinyl group is optionally substituted with one or two $C_1$ to $C_4$ alkyl groups and is optionally in the form of its 4-N-oxide; and $R^{10}$ is H, $C_1$ to $C_3$ alkyl optionally substituted with one or two substituents selected from hydroxy, $NR^5R^6$, $CONR^5R^6$ wherein $R^5$ and $R^6$ are each independently selected from H, $C_1$ to $C_4$ alkyl and $C_3$ alkenyl.

In formula (III), a further group of preferred compounds for use according to the present invention are those wherein: $R^1$ represents H, lower alkyl, Het, alkylHet, or alkylaryl (which latter four groups are all optionally substituted and/or terminated with one or more substituents selected from cyano, lower alkyl, $OR^6$, $C(O)OR^9$ or $NR^{12}R^{13}$); $R^2$ represents H, halo, lower alkyl, Het or aryl (which latter three groups are all optionally substituted and/or terminated with one or more substituents as defined hereinbefore, and preferably with $NR^{12}R^{13}$ or $SO_2NR^{14}R^{15}$); $R^3$ represents $C_1$-$C_4$ alkyl or $C_3$-$C_4$ cycloalkyl which are optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$); $R^4$ represents halo, cyano, nitro, $C(O)R^8$, $C(O)OR^9$, $C(O)NR^{10}R^{11}$, $NR^{12}R^{13}$, $N[Y(O)R^7]_2$, $NR^{16}Y(O)R^{17}$, $SOR^{18}$, $SO_2R^{19}$, $C(O)AZ$, lower alkyl, lower alkynyl, Het or aryl, which latter three groups are all optionally substituted and/or terminated with one or more substituents as defined hereinbefore; and wherein Y, A, Z, $R^{10}$, $R^{11}$, $R^{12}$, $R^{13}$, $R^{14}$, $R^{15}$, $R^{16}$, $R^{17}$, $R^5$, $R^6$, $R^7$, $R^8$, $R^9$, $R^{18}$, $R^{19}$, and Het are as herein before defined. More preferred in this further group are compounds in which $R^1$ represents optionally substituted lower alkyl, more preferably lower alkyl, lower alkoxy-terminated lower alkyl, $NR^{12}R^{13}$-terminated lower alkyl, or N-morpholino-terminated lower alkyl. Alternatively, $R^1$ may represent a 4-piperidinyl or a 3-azetidinyl group, optionally substituted at the nitrogen atom of the piperidinyl group with lower alkyl or $C(O)OR^9$. In such more preferred compounds in this further group $R^2$ represents $C(O)NR^{10}R^{11}$, $NR^{12}R^{13}$, lower alkyl optionally interrupted by one or more of O, S or N, optionally substituted at N by lower alkyl or acyl, or optionally substituted aryl or Het. More preferably, when $R^2$ is interrupted lower alkyl, the interrupting atoms are one or more of O and lower alkylated-N and when $R^2$ is aryl, it is optionally substituted phenyl or pyridyl. Particularly preferred compounds of this further group are those in which $R^2$ represents $C(O)NR^{10}R^{11}$, $NR^{12}R^{11}$, $C_{1-4}$ alkyl optionally interrupted by O or N, optionally substituted at N by lower alkyl, optionally substituted phenyl, or optionally substituted pyridin-2-yl, pyridin-3-yl, pyrimidin-5-yl, pyrazin-2-yl, pyrazol-4-yl, oxadiazol-2-yl, furan-2-yl, furan-3-yl, tetrahydrofuran-2-yl and imidazo[1,2-a]pyridin-6-yl. In this more preferred group of further compounds $R^3$ may represent lower alkyl or cycloalkyl. Also, X is preferably O. Such further and more preferred compounds have $R^4$ representing halo, lower alkyl, lower alkynyl, optionally substituted Het, optionally substituted aryl, $C(O)R^8$, $C(O)AZ$, $C(O)OR^9$, $C(O)NR^{10}R^{11}$, $NR^{12}R^{13}$ or $NR^{16}Y(O)R^{17}$. More preferred values for $R^4$ are $C(O)R^8$ (e.g. acetyl), halo (e.g. iodo), $SO_2R^{19}$ (wherein $R^{19}$ represents lower alkyl) and $C(O)NR^{10}OR^{11}$ (e.g. where $R^{10}$ and $R^{11}$ independently represent H and lower alkyl and/or one of $R^{10}$ and $R^{11}$ is lower alkoxy) or NHB, wherein B represents H, $SO_2CH_3$ or $C(O)Het$. Further preferred still are compounds in which $R^4$ represents iodo, lower alkyl, lower alkynyl (which latter two groups are substituted and/or terminated by $C(O)OR^9$ (wherein $R^9$ represents H or $C_{1-6}$ alkyl)), $N(H)Y(O)R^{17}$, $N[Y(O)R^{17}]_2$, optionally substituted Het or $NR^{12}R^{13}$ (wherein $R^{12}$ and $R^{13}$ together represent $C_{3-5}$ alkylene interrupted by O or N—S$(O)_2$— (optionally substituted aryl)).

More preferred PDEV inhibitors for use with the invention, particularly with an alpha-2-delta ligand selected from gabapentin, pregabalin and (1α,3α,5α)(3-amino-methyl-bicyclo[3.2.0]hept-3-yl)-acetic acid, and pharmaceutically acceptable salts or solvates thereof, are selected from the group:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil);

(6R,12aR)-2,3,6,7,12,12a-hexahydro-2-methyl-6-(3,4-methylenedioxyphenyl)-pyrazino[2',1':6,1]pyrido[3,4-b]indole-1,4-dione (tadalafil, IC-351, Cialis®);

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil);

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one;

5-(5-acetyl-2-butoxy-3-pyridinyl)-3-ethyl-2-(1-ethyl-3-azetidinyl)-2,6-dihydro-7H-pyrazolo[4,3-d]pyrimidin-7-one; and 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine; and pharmaceutically acceptable salts and solvates thereof.

A particularly preferred PDEV inhibitor, particularly with an alpha-2-delta ligand selected from gabapentin, pregabalin and (1α,3α,5α)(3-amino-methyl-bicyclo[3.2.0]hept-3-yl)-acetic acid, and pharmaceutically acceptable salts or solvates thereof, is 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) and pharmaceutically acceptable salts or solvates thereof. Sildenafil citrate is a preferred salt.

As an alternative or further aspect of the present invention, there is provided a combination, particularly a synergistic combination, comprising gabapentin and a PDEV inhibitor selected from sildenafil, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, vardenafil or tadalafil, or a pharmaceutically acceptable salt or solvate thereof. A particularly preferred combination comprises gabapentin and sildenafil or pharmaceutically acceptable salts or solvates thereof.

As an alternative or further aspect of the present invention, there is provided a combination, particularly a synergistic combination, comprising pregabalin and a PDEV inhibitor selected from sildenafil, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, vardenafil or tadalafil. A particularly preferred combination comprises pregabalin and sildenafil.

As a yet further alternative or preferred aspect of the present invention, there is provided a combination, particularly a synergistic combination, comprising [(1R,5R,6S)-6-(Aminomethyl)bicyclo[3.2.0]hept-6-yl]acetic acid or a pharmaceutically acceptable salt or solvate thereof, and a PDEV inhibitor. Suitably, there is provided a combination comprising [(1R,5R,6S)-6-(Aminomethyl)bicyclo[3.2.0]hept-6-yl] acetic acid or a pharmaceutically acceptable salt or solvate thereof, and a PDEV inhibitor selected from sildenafil, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, vardenafil or tadalafil or a pharmaceutically acceptable salt or solvate thereof, preferably sildenafil or a pharmaceutically acceptable salt or solvate thereof.

Suitably, there is provided a combination comprising (1α,3α,5α)(3-amino-methyl-bicyclo[3.2.0]hept-3-yl)-acetic acid or a pharmaceutically acceptable salt or solvate thereof, and a PDEV inhibitor selected from sildenafil, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, vardenafil or tadalafil or a pharmaceutically acceptable salt or solvate thereof, preferably sildenafil or a pharmaceutically acceptable salt or solvate thereof.

As a yet further preferred aspect of the present invention, the combination is selected from:
gabapentin and sildenafil;
gabapentin and vardenafil;
gabapentin and tadalafil;
gabapentin and 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine;
gabapentin and 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one;
pregabalin and sildenafil;
pregabalin and vardenafil;
pregabalin and tadalafil;
pregabalin and 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine;
pregabalin and 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one;
[(1R,5R,6S)-6-(Aminomethyl)bicyclo[3.2.0]hept-6-yl] acetic acid, and sildenafil;
[(1R,5R,6S)-6-(Aminomethyl)bicyclo[3.2.0]hept-6-yl] acetic acid, and vardenafil;
[(1R,5R,6S)-6-(Aminomethyl)bicyclo[3.2.0]hept-6-yl] acetic acid, and tadalafil;
[(1R,5R,6S)-6-(Aminomethyl)bicyclo[3.2.0]hept-6-yl] acetic acid, and 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine; and
[(1R,5R,6S)-6-(Aminomethyl)bicyclo[3.2.0]hept-6-yl] acetic acid, and 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one.
(1α,3α,5α)(3-amino-methyl-bicyclo[3.2.0]hept-3-yl)-acetic acid, and sildenafil;
(1α,3α,5α)(3-amino-methyl-bicyclo[3.2.0]hept-3-yl)-acetic acid, and vardenafil;
(1α,3α,5α)(3-amino-methyl-bicyclo[3.2.0]hept-3-yl)-acetic acid, and tadalafil;
((1α,3α,5α)(3-amino-methyl-bicyclo[3.2.0]hept-3-yl)-acetic acid, and 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine; and (1α,3α,5α)(3-amino-methyl-bicyclo[3.2.0]hept-3-yl)-acetic acid, and 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one;
(3S,4S)-(1-Aminomethyl-3,4-dimethyl-cyclopentyl)-acetic acid, and sildenafil;
(3S,4S)-(1-Aminomethyl-3,4-dimethyl-cyclopentyl)-acetic acid, and vardenafil;

(3S,4S)-(1-Aminomethyl-3,4-dimethyl-cyclopentyl)-acetic acid, and tadalafil;

(3S,4S)-(1-Aminomethyl-3,4-dimethyl-cyclopentyl)-acetic acid, and 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, (3S,4S)-(1-Aminomethyl-3,4-dimethyl-cyclopentyl)-acetic acid, and 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, or pharmaceutically acceptable salts or solvates of any thereof.

The combination of the present invention in a single dosage form is suitable for administration to any mammalian subject, preferably human. Administration may be once (o.d.), twice (b.i.d.) or three times (t.i.d.) daily, suitably b.i.d. or t.i.d., more suitably b.i.d, most suitably o.d. Thus, as a further aspect of the present invention, there is provided a method of curative, prophylactic or palliative treatment of pain in a mammalian subject comprising once, twice or thrice, suitably twice or thrice, more suitably twice, most suitably once daily administration of an effective, particularly synergistic, combination of an alpha-2-delta ligand and a PDEV inhibitor.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients renders impractical the use of this form of testing as a primary model for synergy. However, the observation of synergy in one species can be predictive of the effect in other species and animal models exist, as described herein, to measure a synergistic effect and the results of such studies can also be used to predict effective dose and plasma concentration ratio ranges and the absolute doses and plasma concentrations required in other species by the application of pharmacokinetic/pharmacodynamic methods. Established correlations between animal models and effects seen in man suggest that synergy in animals is best-demonstrated using static and dynamic allodynia measurements in rodents that have undergone surgical (e.g. chronic constriction injury) or chemical (e.g. streptozocin) procedures to induce the allodynia. Because of plateau effects in such models, their value is best assessed in terms of synergistic actions that in neuropathic pain patients would translate to dose-sparing advantages. Other models in which existing agents used for the treatment of neuropathic pain give only a partial response are more suited to predict the potential of combinations acting synergistically to produce increased maximal efficacy at maximally tolerated doses of the two components.

Thus, as a further aspect of the present invention, there is provided a synergistic combination for human administration comprising an alpha-2-delta ligand and a PDEV inhibitor, or pharmaceutically acceptable salts or solvates thereof, in a w/w combination range which corresponds to the absolute ranges observed in a non-human animal model, preferably a rat model, primarily used to identify a synergistic interaction. Suitably, the ratio range in humans corresponds to a non-human range selected from between 1:100 to 100:1 parts by weight, 1:50 to 50:1, 1:50 to 20:1, 1:50 to 10:1, 1:50 to 1:1, 1:20 to 50:1, 1:20 to 20:1, 1:20 to 10:1, 1:20 to 1:1, 1:10 to 50:1, 1:10 to 20:1, 1:10 to 10:1, 1:10 to 1:1, 1:1 to 50:1, 1.1 to 20:1, 1:1 to 10:1 and 50:1 to 100:1. More suitably, the human range corresponds to a synergistic non-human range of 1:10 to 20:1 parts by weight. Preferably, the human range corresponds to a non-human range of the order of 1:1 to 10:1 parts by weight. For gabapentin and sildenafil, the human range corresponds to a synergistic dose range in a non-human, preferably rat, model of the order of 1:1 to 10:1 parts by weight.

For humans, several experimental pain models may be used in man to demonstrate that agents with proven synergy in animals also have effects in man compatible with that synergy. Examples of human models that may be fit for this purpose include the heat/capsaicin model (Petersen, K. L. & Rowbotham, M. C. (1999) NeuroReport 10, 1511-1516), the i.d capsaicin model (Andersen, O. L., Felsby, S., Nicolaisen, L., Bjerring, P., Jsesn, T. S. & Arendt-Nielsen, L. (1996) Pain 66, 51-62), including the use of repeated capsaicin trauma (Witting, N., Svesson, P., Arendt-Nielsen, L. &Jensen, T. S. (2000) Somatosensory Motor Res. 17, 5-12), and summation or wind-up responses (Curatolo, M. et al. (2000) Anesthesiology 93, 1517-1530). With these models, subjective assessment of pain intensity or areas of hyperalgesia may be used as endpoints, or more objective endpoints, reliant on electrophysiological or imaging technologies (such as functional magnetic resonance imaging) may be employed (Bornhovd, K., Quante, M., Glauche, V., Bromm, B., Weiller, C. & Buchel, C. (2002) Brain 125, 1326-1336). All such models require evidence of objective validation before it can be concluded that they provide evidence in man of supporting the synergistic actions of a combination that have been observed in animal studies.

For the present invention in humans, a suitable alpha-2-delta ligand:PDEV inhibitor ratio range is selected from between 1:100 to 100:1 parts by weight, 1:50 to 50:1, 1:50 to 20:1, 1:50 to 10:1, 1:50 to 1:1, 1:20 to 50:1, 1:20 to 20:1, 1:20 to 10:1, 1:20 to 1:1, 1:10 to 50:1, 1:10 to 20:1, 1:10 to 10:1, 1:10 to 1:1, 1:1 to 50:1, 1.1 to 20:1, 1:1 to 10:1 and 100:1 to 50:1, more suitably 1:10 to 20:1, preferably, 1:1 to 10:1. For a combination of gabapentin and sildenafil, the invention provides a suitable dose in the ratio range of 1:10 to 10:1 w/w, more suitably 1:5 to 5:1 respectively.

Optimal doses of each component for synergy can be determined according to published procedures in animal models. However, in man (even in experimental models of pain) the cost can be very high for studies to determine the entire exposure-response relationship at all therapeutically relevant doses of each component of a combination. It may be necessary, at least initially, to estimate whether effects can be observed that are consistent with synergy at doses that have been extrapolated from those that give optimal synergy in animals. In scaling the doses from animals to man, factors such as relative body weight/body surface area, relative absorption, distribution, metabolism and excretion of each component and relative plasma protein binding need to be considered and, for these reasons, the optimal dose ratio predicted for man (and also for patients) is unlikely to be the same as the dose ratio shown to be optimal in animals. However, the relationship between the two can be understood and calculated by one skilled in the art of animal and human pharmacokinetics. Important in establishing the bridge between animal and human effects are the plasma concentrations obtained for each component used in the animal studies, as these are related to the plasma concentration of each component that would be expected to provide efficacy in man. Pharmacokinetic/pharmacodynamic modeling (including methods such as isobolograms, interaction index and response surface modelling) and simulations may help to predict synergistic dose ratios in man, particularly where either or both of these components has already been studied in man.

It is important to ascertain whether any concluded synergy observed in animals or man is due solely to pharmacokinetic interactions. For example, inhibition of the metabolism of one compound by another might give a false impression of pharmacodynamic synergy. In animal studies with gabapentin and sildenafil, repeated blood samples have been taken and it has been shown that, in accordance with the known pharmacokinetic properties of the agents, there is no evidence of any pharmacokinetic interaction when the compounds are administered at the doses that induced synergistic pain interactions. This proves that the synergy with respect to pain is pharmacodynamic, occurring subsequent to each of these agents interacting with their respective receptor and/or enzyme targets.

Thus, according to a further aspect of the present invention, there is provided a synergistic combination for administration to humans comprising an alpha-2-delta ligand and a PDEV inhibitor or pharmaceutically acceptable salts or solvates thereof, where the dose range of each component corresponds to the absolute synergistic ranges observed in a non-human animal model, preferably the rat model, primarily used to identify a synergistic interaction. Suitably, the dose range of alpha-2-delta ligand in human corresponds to a dose range of 1-20 mg/kg, more suitably 1-10 mg/kg, in the rat and the corresponding dose range for a PDEV inhibitor is 0.1-10 mg/kg, more suitably 0.1-1 mg/kg. For gabapentin and sildenafil, the dose range in the human suitably corresponds to a synergistic range of 1-10 mg/kg gabapentin and 0.1-1 mg/kg sildenafil in the rat.

Suitably, the dose of alpha-2-delta ligand for use in a human is in a range selected from 1-1200 mg, 1-500 mg, 1-100 mg, 1-50 mg, 1-25 mg, 500-1200 mg, 100-1200 mg, 100-500 mg, 50-1200 mg, 50-500 mg, or 50-100 mg, suitably 50-100 mg, b.i.d. or t.i.d., suitably t.i.d., and the dose of PDEV inhibitor is in a range selected from 1-200 mg, 1-100 mg, 1-50 mg, 1-25 mg, 10-100 mg, 10-50 mg or 10-25 mg, suitably 10-100 mg, b.i.d or t.i.d, suitably t.i.d. For gabapentin and sildenafil, the suitable dose ranges are 50-600 mg:10-100 mg t.i.d.

It will be apparent to the skilled reader that the plasma concentration ranges of the alpha-2-delta ligand and PDEV inhibitor combinations of the present invention required to provide a therapeutic effect depend on the species to be treated, and components used. For example, for gabapentin and sildenafil in the rat the Cmax values of gabapentin range from 0.520 µg/ml to 10.5 µg/ml and the Cmax values of sildenafil range from 0.02 µg/ml to 2.1 µg/ml.

It is possible, using standard PK/PD and allometric methods, to extrapolate the plasma concentration values observed in an animal model to predict the values in a different species, particularly human. Thus, as a further aspect of the present invention, there is provided a synergistic combination for administration to humans comprising an alpha-2-delta ligand and a PDEV inhibitor, where the plasma concentration range of each component corresponds to the absolute ranges observed in a non-human animal model, preferably the rat model, primarily used to identify a synergistic interaction. Suitably, the plasma concentration range in the human corresponds to a range of 0.05 µg/ml to 10.5 µg/ml for an alpha-2-delta ligand and 0.005 µg/ml to 2.1 µg/ml for a PDEV inhibitor in the rat model. For gabapentin and sildenafil, the plasma concentration range in the human corresponds to a range of 0.05 µg/ml to 10.5 µg/ml for gabapentin and 0.005 µg/ml to 2.1 µg/ml for sildenafil in the rat model. Since protein-binding properties are similar in rat and human plasma for both compounds, the plasma concentration ranges above are relevant to human.

Thus, an alternative aspect, the present invention provides a synergistic combination comprising an alpha-2-delta ligand and a PDEV inhibitor, or pharmaceutically acceptable salts or solvates thereof, where the plasma concentration range for the components comprises Cmax values of up to 20 µg/ml for the alpha-2-delta ligand and up to 4 µg/ml for a PDEV inhibitor, more suitably 0.5 µg/ml to 10 µg/ml and 0.02 µg/ml to 2.1 µg/ml, preferably 0.05 µg/ml to 20 µg/ml and 0.005 µg/ml to 4 µg/ml respectively.

Particularly preferred combinations of the invention include those in which each variable of the combination is selected from the suitable parameters for each variable. Even more preferable combinations of the invention include those where each variable of the combination is selected from the more suitable, most suitable, preferred or more preferred parameters for each variable.

BRIEF DECRIPTION OF THE DRAWINGS

FIG. 1. Effect of (a) gabapentin and (b) sildenafil on the maintenance of CCI-induced static allodynia. Baseline (BL) paw withdrawal thresholds (PWT) to von Frey hairs were determined in CCI animals before drug administration. PWT were re-examined up to 4 h post drug. Results are expressed as median force (g) required to induce paw withdrawal (vertical bars represent $1^{st}$ and $3^{rd}$ quartiles). *P<0.05 P<0.01 *P<0.005 significantly different (Mann Whitney U test) from vehicle treated group at each time point.

Figure 2:
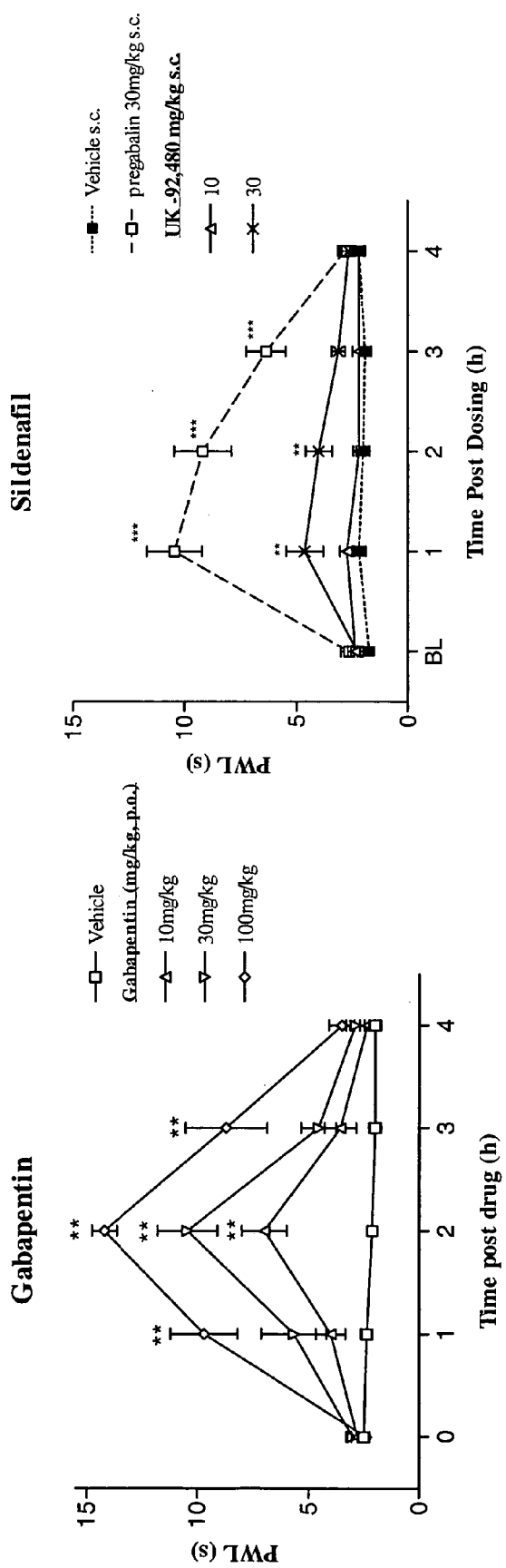

FIG. 2. Effect of (a) gabapentin and (b) sildenafil on the maintenance of CCI-induced dynamic allodynia. Baseline (BL) paw withdrawal latencies (PWL) to cotton bud stimulus were determined for right hind paw before drug administration. PWL's were re-examined for up to 4 hours. Results are expressed as mean PWL (s) vertical bars represent ±SEM *P<0.05, **P<0.01, Significantly different (ANOVA followed by a Dunnett's t-test) from vehicle treated group at each time point.

Figure 3:
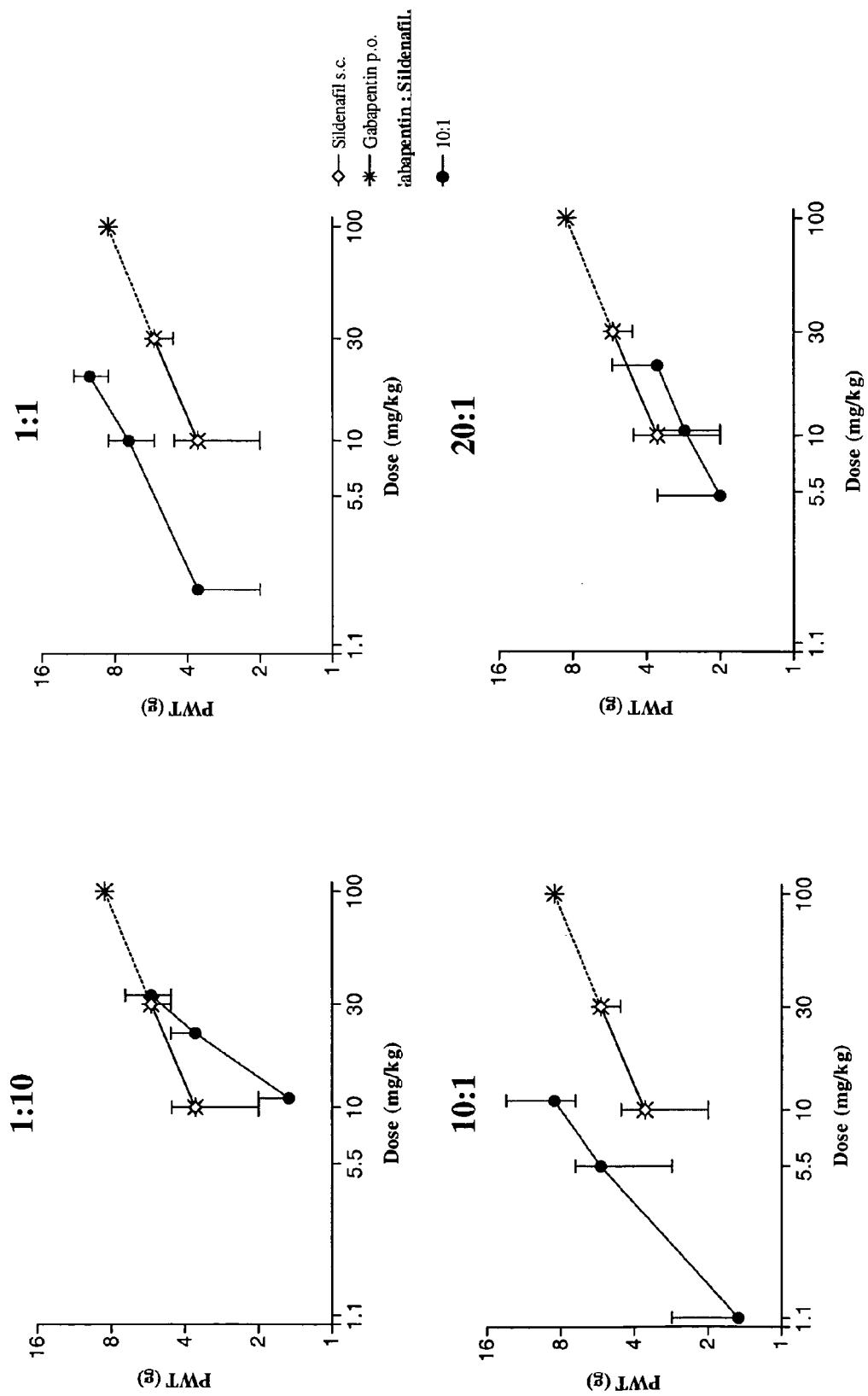

FIG. 3. Effect of fixed dose ratios of gabapentin and sildenafil on the maintenance of CCI-induced static allodynia. All data is expressed at the 2 h time point post drug administration. Dose-response data for gabapentin and sildenafil alone were taken from FIG. 1. Fixed dose ratios of (a) 1:10 (b) 1:1 (c) 10:1 (d) 20:1 gabapentin and sildenafil combinations. Results are expressed as median force (g) required to induce paw withdrawal (vertical bars represent $1^{st}$ and $3^{rd}$ quartiles).

Figure 4:
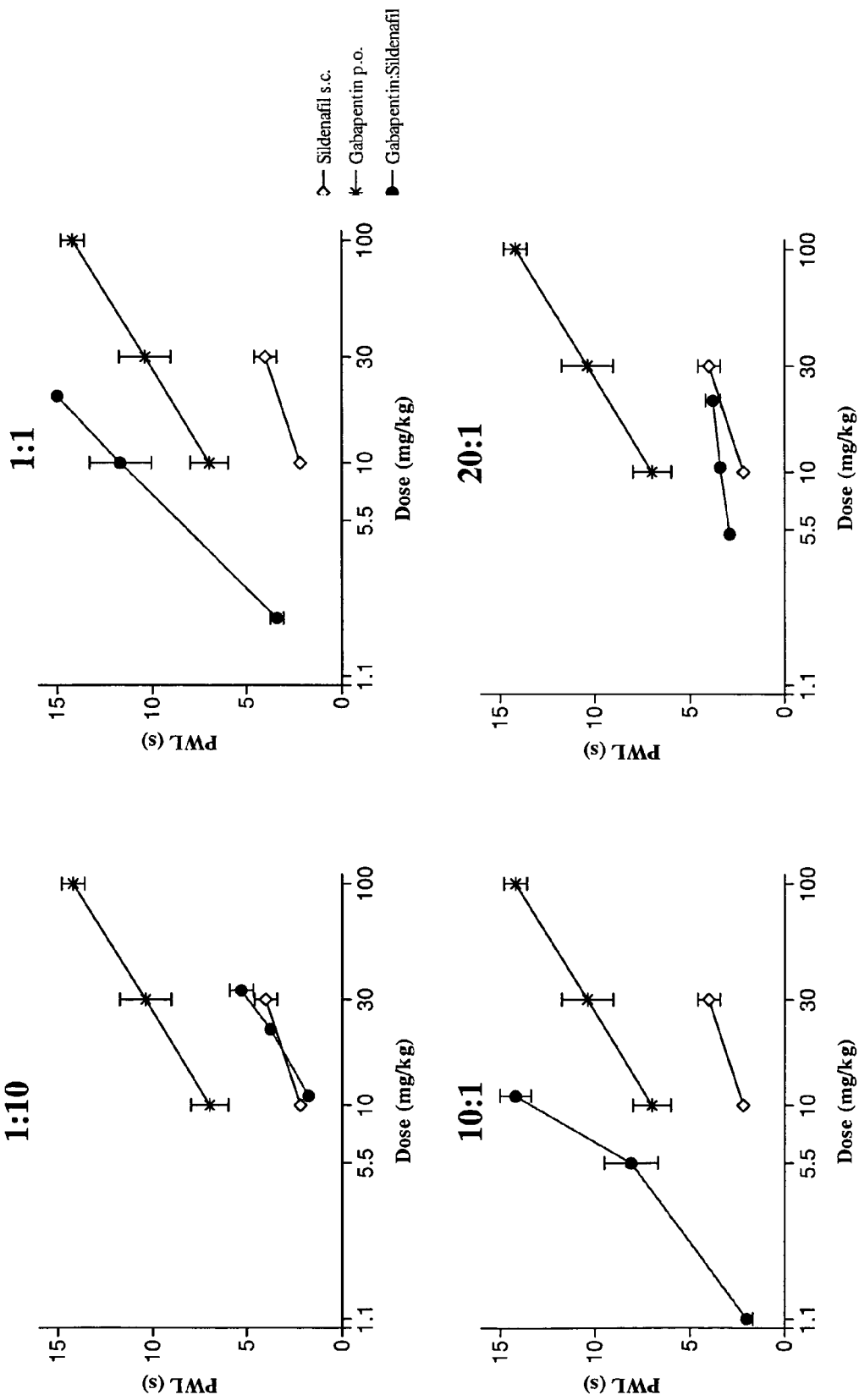

FIG. 4. Effect of fixed dose ratios of gabapentin and sildenafil on the maintenance of CCI-induced dynamic allodynia. All data is expressed at the 2 h time point post drug administration. Dose-response data for gabapentin and sildenafil alone were taken from FIG. 2. Fixed dose ratios of (a) 1:10 (b) 1:1 (c) 10:1 (d) 20:1 gabapentin and sildenafil combinations. Results are expressed as mean PWL (s) vertical bars represent ±SEM *P<0.05, **P<0.01, Significantly different (ANOVA followed by a Dunnett's t-test) from vehicle treated group at each time point.

DETAILED DESCRIPTION OF THE INVENTION

The compounds of the present combination invention can exist in unsolvated forms as well as solvated forms, including hydrated forms. In general, the solvated forms, including hydrated forms, which may contain isotopic substitutions (e.g. D20, d6-acetone, d6-DMSO), are equivalent to unsolvated forms and are encompassed within the scope of the present invention.

Certain of the compounds of the present invention possess one or more chiral centers and each center may exist in the R or S configuration. The present invention includes all enantiomeric and epimeric forms as well as the appropriate mixtures thereof. Separation of diastereoisomers or cis and trans isomers may be achieved by conventional techniques, e.g. by fractional crystallisation, chromatography or H.P.L.C. of a stereoisomeric mixture of a compound of the invention or a suitable salt or derivative thereof.

A number of alpha-2-delta ligands of the present invention are amino acids. Since amino acids are amphoteric, pharmacologically compatible salts can be salts of appropriate non-toxic inorganic or organic acids or bases. Suitable acid addition salts are the acetate, aspartate, benzoate, besylate, bicarbonate/carbonate, bisulphate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, palmoate, phosphate, saccharate, stearate, succinate sulphate, D- and L-tartrate, and tosylate salts. Suitable base salts are formed from bases which form non-toxic salts and examples are the sodium, potassium, aluminium, calcium, magnesium, zinc, choline, diolamine, olamine, arginine, glycine, tromethamine, benzathine, lysine, meglumine and diethylamine salts. Salts with quaternary ammonium ions can also be prepared with, for example, the tetramethyl-ammonium ion. The compounds of the invention may also be formed as a zwitterion. Furthermore, since a number of the PDEV inhibitors of the present invention are amines and a number of the alpha-2-delta ligands have an acid functionality, a further aspect of the present invention comprises a salt form containing the 2 components, particularly in a 1:1 combination. A suitable combination salt form is the salt formed by a 1:1 combination of gabapentin and sildenafil.

A suitable salt for amino acid compounds of the present invention is the hydrochloride salt. For a review on suitable salts see Stahl and Wermuth, Handbook of Pharmaceutical Salts: Properties, Selection, and Use, Wiley-VCH, Weinheim, Germany (2002).

Also within the scope of the invention are clathrates, drug-host inclusion complexes wherein, in contrast to the aforementioned solvates, the drug and host are present in non-stoichiometric amounts. For a review of such complexes, see J Pharm Sci, 64 (8), 1269-1288 by Haleblian (August 1975).

Hereinafter all references to compounds of the invention include references to salts thereof and to solvates and clathrates of compounds of the invention and salts thereof.

Also included within the present scope of the compounds of the invention are polymorphs thereof.

Prodrugs of the above compounds of the invention are included in the scope of the instant invention. The chemically modified drug, or prodrug, should have a different pharmacokinetic profile to the parent, enabling easier absorption across the mucosal epithelium, better salt formulation and/or solubility, improved systemic stability (for an increase in plasma half-life, for example). These chemical modifications may be (1) Ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.

(2) Peptides which may be recognized by specific or non-specific proteinases. A peptide may be coupled to the drug molecule via amide bond formation with the amine or carboxylic acid moiety of the drug molecule by known means.

(3) Derivatives that accumulate at a site of action through membrane selection of a prodrug form or modified prodrug form.

(4) Any combination of 1 to 3.

Aminoacyl-glycolic and -lactic esters are known as prodrugs of amino acids (Wermuth C. G., *Chemistry and Industry*, 1980:433-435). The carbonyl group of the amino acids can be esterified by known means. Prodrugs and soft drugs are known in the art (Palomino E., *Drugs of the Future*, 1990;15(4):361-368). The last two citations are hereby incorporated by reference.

The combination of the present invention is useful for the general treatment of pain, particularly neuropathic pain. Physiological pain is an important protective mechanism designed to warn of danger from potentially injurious stimuli from the external environment. The system operates through a specific set of primary sensory neurones and is exclusively activated by noxious stimuli via peripheral transducing mechanisms (Millan 1999 Prog. Neurobio. 57: 1-164 for an integrative Review). These sensory fibres are known as nociceptors and are characterised by small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred after complex processing in the dorsal horn, either directly or via brain stem relay nuclei to the ventrobasal thalamus and then on to the cortex, where the sensation of pain is generated.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765-1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13-44). Although patients with back pain, arthritis pain, CNS trauma, or neuropathic pain may have similar symptoms, the underlying mechanisms are different and, therefore, may require different treatment strategies. Therefore pain can be divided into a number of different areas because of differing pathophysiology, these include nociceptive, inflammatory, neuropathic pain etc. It should be noted that some types of pain have multiple aetiologies and thus can be classified in more than one area, e.g. Back pain, Cancer pain can have nociceptive inflammatory and neuropathic components.

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13-44). The activation of nociceptors activates two types of afferent nerve fibres. Myelinated A-delta fibres transmitted rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertebral discs or abnormalities of the lumber facet joints, sacroiliac joints, paraspinal muscles or the posterior longitudinal ligament Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, diabetic neuropathy, post herpetic neuralgia, back pain, cancer neuropathy, chemotherapy-induced neuropathy, HIV neuropathy, Phantom limb pain, Carpal Tunnel Syndrome, chronic alcoholism, hypothyroidism, trigeminal neuralgia, uremia, trauma-induced neuropathy, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959-1964). The symptoms of neuropathic pain are difficult to treat, as they are often heterogeneous even between patients with the same disease (Woolf & Decosterd 1999 Pain Supp. 6: S141-S147; Woolf and Mannion 1999 Lancet 353: 1959-1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

The inflammatory process is a complex series of biochemical and cellular events activated in response to tissue injury or the presence of foreign substances, which result in swelling and pain (Levine and Taiwo 1994: Textbook of Pain 45-56). Arthritic pain makes up the majority of the inflammatory pain population. Rheumatoid disease is one of the commonest chronic inflammatory conditions in developed countries and rheumatoid arthritis (RA) is a common cause of disability. The exact aetiology of RA is unknown, but current hypotheses suggest that both genetic and microbiological factors may be important (Grennan & Jayson 1994 Textbook of Pain 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder 2002 Ann Pharmacother. 36: 679-686; McCarthy et al., 1994 Textbook of Pain 387-395). Most patients with OA seek medical attention because of pain. Arthritis has a significant impact on psychosocial and physical function and is known to be the leading cause of disability in later life. Other types of inflammatory pain include but are not limited to inflammatory bowel diseases (IBD), Other types of pain include but are not limited to;

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis.

Central pain or 'thalamic pain' as defined by pain caused by lesion or dysfunction of the nervous system including but not limited to central post-stroke pain, multiple sclerosis, spinal cord injury, Parkinson's disease and epilepsy.

Heart and vascular pain including but not limited to angina, myocardial infarction, mitral stenosis, pericarditis, Raynaud's phenomenon, sclerodoma, skeletal muscle ischemia.

Visceral pain, and gastrointestinal disorders. The viscera encompasses the organs of the abdominal cavity. These organs include the sex organs, spleen and part of the digestive system. Pain associated with the viscera may be neuropathic, nociceptive as well as inflammatory and can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis.

Head pain including but not limited to migraine, migraine with aura, migraine without aura, cluster headache, tension-type headache.

Orofacial pain including but not limited to dental pain, temporomandibular myofascial pain.

Thus, as a yet further aspect, there is provided the simultaneous, sequential or separate use of an alpha-2-delta ligand, excluding compounds of formula (i)-(xxv) of PCT/IB02/01146 and pregabalin or gabapentin, where the exclusion of pregabalin or gabapentin is limited to use in the treatment of neuropathy, and a PDEV inhibitor in the manufacture of a medicament for the curative, prophylactic or palliative treatment of pain, particularly neuropathic pain. As a preferred feature, the use suitably comprises any one of the combinations mentioned herein above.

As an alternative aspect, there is provided a method for the curative, prophylactic or palliative treatment of pain, particularly neuropathic pain, comprising simultaneous, sequential or separate administration of a therapeutically effective amount of an alpha-2-delta ligand, excluding pregabalin or gabapentin, where the exclusion of pregabalin or gabapentin is limited to use in the treatment of neuropathy, and a PDEV inhibitor to a mammal in need of said treatment. As an alternative aspect, the exclusion may the include compounds of formula (i)-(xxv) of PCT/IB02/01146. As a preferred feature, the method suitably comprises any one of the combinations mentioned herein above.

As an alternative aspect, there is provided the simultaneous, sequential or separate use of a synergistic combination of an alpha-2-delta ligand and a PDEV inhibitor in the manufacture of a medicament for the curative, prophylactic or palliative treatment of pain, particularly neuropathic pain. As a preferred feature, the use suitably comprises any one of the combinations mentioned herein above.

As a further alternative aspect, there is provided a method for the curative, prophylactic or palliative treatment of pain, particularly neuropathic pain, comprising simultaneous, sequential or separate administration of a therapeutically synergistic amount of an alpha-2-delta ligand and a PDEV inhibitor to a mammal in need of said treatment. As a preferred feature, the method suitably comprises any one of the combinations mentioned herein above.

The biological activity of the alpha-2-delta ligands of the invention may be measured in a radioligand binding assay using [$^3$H]gabapentin and the $\alpha_2\delta$ subunit derived from porcine brain tissue (Gee N. S., Brown J. P., Dissanayake V. U. K., Offord J., Thurlow R., Woodruff G. N., *J. Biol. Chem.*, 1996;271:5879-5776). Results may be expressed in terms of μM or nM $\alpha 2\delta$ binding affinity.

In vitro inhibitory activities of the PDEV inhibitors of the present invention against cyclic guanosine monophosphate (cGMP) may be determined by measurement of their $IC_{50}$ values, according to the details described in WO01/27113. Functional activity can be assessed as described by S A Ballard et al (Brit. J. Pharmacology, 1996, 118 (suppl.), abstract 153P).

The elements of the combination of the instant invention may be administered separately, simultaneously or sequentially. As a further aspect of the present invention, there is provided a package comprising a synergistic combination of an alpha-2-delta ligand and a PDEV inhibitor and a suitable container.

The combination of the present invention may also optionally be administered with one or more other pharmacologically active agents. Suitable optional agents include:

(i) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, buprenorphine, butorphanol, nalbuphine and pentazocine;

(ii) Opioid antagonists, e.g. naloxone, naltrexone (iii) nonsteroidal antiinflammatory drugs (NSAIDs), e.g. aspirin, diclofenac, difluinsal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and their pharmaceutically acceptable salts or solvates;

(iv) barbiturate sedatives, e.g. amobarbital, aprobarbital, butabarbital, butabital, mephobarbital, metharbital, methohexital, pentobarbital, phenobartital, secobarbital, talbutal, theamylal, thiopental and their pharmaceutically acceptable salts or solvates;

(v) benzodiazepines having a sedative action, e.g. chlordiazepoxide, clorazepate, diazepam, flurazepam, lorazepam, oxazepam, temazepam, triazolam and their pharmaceutically acceptable salts or solvates, (vi) $H_1$ antagonists having a sedative action, e.g. diphenhydramine, pyrilamine, promethazine, chlorpheniramine, chlorcyclizine and their pharmaceutically acceptable salts or solvates;

(vii) miscellaneous sedatives such as glutethimide, meprobamate, methaqualone, dichloralphenazone and their pharmaceutically acceptable salts or solvates;

(viii) skeletal muscle relaxants, e.g. baclofen, tolperisone, carisoprodol, chlorzoxazone, cyclobenzaprine, methocarbamol, orphrenadine and their pharmaceutically acceptable salts or solvates, (ix) NMDA receptor antagonists, e.g. dextromethorphan ((+)-3-hydroxy-N-methylmorphinan) and its metabolite dextrorphan ((+)-3-hydroxy-N-methylmorphinan), ketamine, memantine, pyrroloquinoline quinone and cis-4-(phosphonomethyl)-2-piperidinecarboxylic acid and their pharmaceutically acceptable salts or solvates;

(x) alpha-adrenergic active compounds, e.g. doxazosin, tamsulosin, clonidine and 4-amino-6,7-dimethoxy-2-(5-methanesulfonamido-1,2,3,4-tetrahydroisoquinol-2-yl)-5-(2-pyridyl) quinazoline;

(xi) tricyclic antidepressants, e.g. desipramine, imipramine, amytriptiline and nortriptiline;

(xii) anticonvulsants, e.g. carbamazepine, valproate, lamotrigine;

(xiii) serotonin reuptake inhibitors, e.g. fluoxetine, paroxetine, citalopram and sertraline;

(xiv) mixed serotonin-noradrenaline reuptake inhibitors, e.g. milnacipran, venlafaxine and duloxetine;

(xv) noradrenaline reuptake inhibitors , e.g. reboxetine;

(xvi) Tachykinin (NK) antagonists, particularly Nk-3, NK-2 and NK-1 antagonists e.g., ($\alpha$R,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S)

(xvii) Muscarinic antagonists, e.g oxybutin, tolterodine, propiverine, tropsium chloride and darifenacin;

(xviii) COX-2 inhibitors, e.g. celecoxib, rofecoxib and valdecoxib;

(xix) Non-selective COX inhibitors (preferably with GI protection), e.g. nitroflurbiprofen (HCT-1026);

(xx) coal-tar analgesics, in particular, paracetamol;

(xxi) neuroleptics, such as droperidol;

(xxii) Vanilloid receptor agonists, e.g. resinferatoxin;

(xxiii) Beta-adrenergic compounds such as propranolol;

(xxiv) Local anaesthetics, such as mexiletine, lidocaine;

(xxv) Corticosteriods, such as dexamethasone (xxvi) serotonin receptor agonists and antagonists;

(xxvii) cholinergic (nicotinic) analgesics; and (xxviii) miscellaneous agents such as Tramadol®.

Thus, the present invention extends to a combination product comprising an alpha-2-delta ligand, a PDEV inhibitor, and one or more other therapeutic agents, such as one of those listed above, for simultaneous, separate or sequential use in the curative, prophylactic or palliative treatment of pain, particularly neuropathic pain.

The combination of the invention can be administered alone but one or both elements will generally be administered in an admixture with suitable pharmaceutical excipient(s), diluent(s) or carrier(s) selected with regard to the intended route of administration and standard pharmaceutical practice. If appropriate, auxiliaries can be added. Auxiliaries are preservatives, anti-oxidants, flavours or colourants. The compositions of the invention may be of immediate-, delayed-, modified-, sustained-, pulsed- or controlled-release type. For example, WO0024383 describes controlled-release oral pharmaceutical formulations of cGMP PDE-5 inhibitors, including sildenafil, the contents of which is incorporated herein.

The elements of the combination of the present invention can be administered, for example but not limited to, the following route: orally, buccally or sublingually in the form of tablets, capsules, multi-and nano-particulates, gels, films (incl. muco-adhesive), powder, ovules, elixirs, lozenges (incl. liquid-filled), chews, solutions, suspensions and sprays. The compounds of the combination may also be administered as osmotic dosage form, or in the form of a high energy dispersion or as coated particles or fast-dissolving, fast-disintegrating dosage form as described in Ashley Publications, 2001 by Liang and Chen. The compounds of the combination may be administered as crystalline or amorphous products, freeze dried or spray dried. Suitable formulations of the compounds of the invention may be in hydrophilic or hydrophobic matrix, ion-exchange resin complex, coated or uncoated form and other types as described in U.S. Pat. No. 6,106,864 as desired. Such pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), mannitol, disintegrants such as sodium starch glycolate, crosscarmellose sodium and certain complex silicates, and granulation binders such as polyvinylpyrrolidone, hydroxypropylmethylcellulose (HPMC), triglycerides, hydroxypropylcellulose (HPC), bentonite sucrose, sorbitol, gelatin and acacia. Additionally, lubricating agents may be added to solid compositions such as magnesium stearate, stearic acid, glyceryl behenate, PEG and talc or wetting agents, such as sodium lauryl sulphate. Additionally, polymers such as carbohydrates, phospoholipids and proteins may be included.

Fast dispersing or dissolving dosage fromulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol or xylitol. The terms dispersing or dissolving as used herein to describe FDDFs are dependent upon the solubility of the drug substance used, i.e. where the drug substance is insoluble a fast dispersing dosage form can be prepared and where the drug substance is soluble a fast dissolving dosage form can be prepared.

The solid dosage form, such as tablets are manufactured by a standard process, for example, direct compression or a wet, dry or melt granulation, melt congealing and extrusion process. The tablet cores which may be mono or multi-layer may be coated with appropriate overcoats known in the art.

Solid compositions of a similar type may also be employed as fillers in capsules such as gelatin, starch or HPMC capsules. Preferred excipients in this regard include lactose, starch, a cellulose, milk sugar or high molecular weight polyethylene glycols. Liquid compositions may be employed as fillers in soft or hard capsules such as gelatin capsule. For aqueous and oily suspensions, solutions, syrups and/or elixirs, the compounds of the invention may be combined with various sweetening or flavouring agents, colouring matter or dyes, with emulsifying and/or suspending agents and with diluents such as water, ethanol, propylene glycol, methylcellulose, alginic acid or sodium alginate, glycerin, oils, hydrocolloid agents and combinations thereof. Moreover, formulations containing these compounds and excipients may be presented as a dry product for constitution with water or other suitable vehicles before use.

Liquid form preparations include solutions, suspensions, and emulsions, for example, water or water propylene glycol solutions. For parenteral injection, liquid preparations can be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

The elements of the combination of the present invention can also be administered by injection, that is, intravenously, intramuscularly, intracutaneously, intraduodenally, or intraperitoneally, intraarterially, intrathecally, intraventricularly, intraurethrally, intrasternally, intracranially, intraspinally or subcutaneously, or they may be administered by infusion, needle-free injectors or implant injection techniques. For such parenteral administration they are best used in the form of a sterile aqueous solution, suspension or emulsion (or system so that can include micelles) which may contain other substances known in the art, for example, enough salts or carbohydrates such as glucose to make the solution isotonic with blood. The aqueous solutions should be suitably buffered (preferably to a pH of from 3 to 9), if necessary. For some forms of parenteral administration they may be used in the form of a sterile non-aqueous system such as fixed oils, including mono- or diglycerides, and fatty acids, including oleic acid. The preparation of suitable parenteral formulations under sterile conditions for example lyophilisation is readily accomplished by standard pharmaceutical techniques well-known to those skilled in the art. Alternatively, the active ingredient may be in powder form for constitution with a suitable vehicle (e.g. sterile, pyrogen-free water) before use.

Also, the elements of the combination of the present invention can be administered intranasally or by inhalation. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomiser (preferably an atomiser using electrohydrodynamics to produce a fine mist) or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide, a further perfluorinated hydrocarbon such as Perflubron (trade mark) or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol (optionally, aqueous ethanol) or a suitable agent for dispersing, solubilising or extending release and the propellant as the solvent, which may additionally contain a lubricant, e.g. sorbitan trioleate. Capsules, blisters and cartridges (made, for example, from gelatin or HPMC) for use in an inhaler or insufflator may be formulated to contain a powder mix of the compound of the invention, a suitable powder base such as lactose or starch and a performance modifier such as l-leucine, mannitol or magnesium stearate.

Prior to use in a dry powder formulation or suspension formulation for inhalation the elements of the combination of the invention will be micronised to a size suitable for delivery by inhalation (typically considered as less than 5 microns). Micronisation could be achieved by a range of methods, for example spiral jet milling, fluid bed jet milling, use of supercritical fluid crystallisation or by spray drying.

A suitable solution formulation for use in an atomiser using electrohydrodynamics to produce a fine mist may contain from 1 μg to 10 mg of the compound of the invention per actuation and the actuation volume may vary from 1 to 100 μl. A typical formulation may comprise a compound of the invention, propylene glycol, sterile water, ethanol and sodium chloride. Alternative solvents may be used in place of propylene glycol, for example glycerol or polyethylene glycol.

Alternatively, the elements of the combination of the invention may be administered topically to the skin, mucosa, dermally or transdermally, for example, in the form of a gel, hydrogel, lotion, solution, cream, ointment, dusting powder, dressing, foam, film, skin patch, wafers, implant, sponges, fibres, bandage, microemulsions and combinations thereof. For such applications, the compounds of the invention can be suspended or dissolved in, for example, a mixture with one or more of the following: mineral oil, liquid petrolatum, white petrolatum, propylene glycol, polyoxyethylene polyoxypropylene compound, emulsifying wax, fixed oils, including synthetic mono- or diglycerides, and fatty acids, including oleic acid, water, sorbitan monostearate, a polyethylene glycol, liquid paraffin, polysorbate 60, cetyl esters wax, cetearyl alcohol, 2-octyldodecanol, benzyl alcohol, alcohols such as ethanol. Alternatively, penetration enhancers may be used. The following may also be used polymers, carbohydrates, proteins, phospholipids in the form of nanoparticles (such as niosomes or liposomes) or suspended or dissolved. In addition, they may be delivered using iontophoresis, electroporation, phonophoresis and sonophoresis.

Alternatively, the elements of the combination of the invention can be administered rectally, for example in the form of a suppository or pessary. They may also be administered by vaginal route. For example, these compositions may be prepared by mixing the drug with a suitable non-irritant excipients, such as cocoa butter, synthetic glyceride esters or polyethylene glycols, which are solid at ordinary temperatures, but liquefy and/or dissolve in the cavity to release the drug.

The elements of the combination of the invention may also be administered by the ocular route. For ophthalmic use, the compounds can be formulated as micronised suspensions in isotonic, pH adjusted, sterile saline, or, preferably, as solutions in isotonic, pH adjusted, sterile saline. A polymer may be added such as crossed-linked polyacrylic acid, polyvinylalcohol, hyaluronic acid, a cellulosic polymer (e.g. hydroxypropylmethylcellulose, hydroxyethylcellulose, methyl cellulose), or a heteropolysaccharide polymer (e.g. gelan gum). Alternatively, they may be formulated in an ointment such as petrolatum or mineral oil, incorporated into bio-degradable (e.g. absorbable gel sponges, collagen) or non-biodegradable (e.g. silicone) implants, wafers, drops, lenses or delivered via particulate or vesicular systems such as niosomes or liposomes. Formulations may be optionally combined with a preservative, such as benzalkonium chloride. In addition, they may be delivered using iontophoresis. They may also be administered in the ear, using for example but not limited to the drops.

The elements of the combination of the invention may also be used in combination with a cyclodextrin. Cyclodextrins are known to form inclusion and non-inclusion complexes with drug molecules. Formation of a drug-cyclodextrin complex may modify the solubility, dissolution rate, taste-masking, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The term 'administered' includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, lipsomes, immunoliposomes, lipofectin, cationic facial amphiphiles (CFAs) and combinations thereof. The routes for such delivery mechanisms include but are not limited to mucosal, nasal, oral, parenteral, gastrointestinal, topical or sublingual routes.

Thus, as a further aspect of the present invention, there is provided a pharmaceutical composition comprising a combination comprising an alpha-2-delta ligand, excluding gabapentin, pregabalin, a PDEV inhibitor and a suitable excipient, diluent or carrier. Alternatively, the exclusion may include the compounds of formula (i)-(xxv) of PCT/IB02/01146. Suitably, the composition is suitable for use in the treatment of pain, particularly neuropathic pain.

As an alternative aspect of the present invention, there is provided a pharmaceutical composition comprising a synergistic combination comprising an alpha-2-delta ligand, a PDEV inhibitor and a suitable excipient, diluent or carrier. Suitably, the composition is suitable for use in the treatment of pain, particularly neuropathic pain.

For non-human animal administration the term 'pharmaceutical' as used herein may be replaced by 'veterinary'.

The element of the pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form. The quantity of active component in a unit dose preparation may be varied or adjusted according to the particular application and the potency of the active components. Generally, treatment is initiated with smaller dosages which are less than the optimum dose of the compounds. Thereafter, the dosage is increased by small increments until the optimum effect under the circumstances is reached. For convenience, the total daily dosage may be divided and administered in portions during the day, if desired.

For veterinary use, a combination according o the present invention or veterinarily acceptable salts or solvates thereof, is administered as a suitably acceptable formulation in accordance with normal veterinary practice and the veterinary surgeon will determine the dosing regimen and route of administration which will be most appropriate for a particular animal.

BIOLOGY EXAMPLES

Methods

Animals

Male Sprague Dawley rats (200-250 g), obtained from Charles River, (Margate, Kent, U.K.) were housed in groups of 6. All animals were kept under a 12 h light/dark cycle (lights on at 07 h 00 min) with food and water ad libitum. All experiments were carried out by an observer unaware of drug treatments.

CCI Surgery in the Rat

Animals were anaesthetised with isoflurane. The sciatic nerve was ligated as previously described by Bennett and Xie, 1988. Animals were placed on a homeothermic blanket for the duration of the procedure. After surgical preparation the common sciatic nerve was exposed at the middle of the thigh by blunt dissection through biceps femoris. Proximal to the sciatic trifurcation, about 7 mm of nerve was freed of adhering tissue and 4 ligatures (4-0 silk) were tied loosely around it with about 1 mm spacing. The incision was closed in layers and the wound treated with topical antibiotics.

Effect of Combinations on the Maintenance of CCI-Induced Static and Dynamic Allodynia Dose-responses to gabapentin and sildenafil were first performed alone in the CCI model. Combinations were examined following a fixed ratio design. A dose-response to each fixed dose ratio of the combination was performed. On each test day, baseline paw withdrawal thresholds (PWT) to von Frey hairs and paw withdrawal latencies (PWL) to a cotton bud stimulus were determined prior to drug treatment. Gabapentin was administered p.o. directly followed by s.c. administration of sildenafil and PWT and PWL re-examined for up to 5 h. The data are expressed at the 2 h time point for both the static and dynamic data as this timepoint represent the peak antiallodynic effects.

Evaluation of Allodynia

Static allodynia was measured using Semmes-Weinstein von Frey hairs (Stoelting, Illinois, U.S.A.). Animals were placed into wire mesh bottom cages allowing access to the underside of their paws. Animals were habituated to this environment prior to the start of the experiment. Static allodynia was tested by touching the plantar surface of the animals right hind paw with von Frey hairs in ascending order of force (0.7, 1.2, 1.5, 2, 3.6, 5.5, 8.5, 11.8, 15.1 and 29 g) for up to 6 sec. Once a withdrawal response was established, the paw was re-tested, starting with the next descending von Frey hair until no response occurred. The highest force of 29 g lifted the paw as well as eliciting a response, thus represented the cut off point. The lowest amount of force required to elicit a response was recorded as the PWT in grams.

Dynamic allodynia was assessed by lightly stroking the plantar surface of the hind paw with a cotton bud. Care was taken to perform this procedure in fully habituated rats that were not active to avoid recording general motor activity. At least three measurements were taken at each time point the mean of which represented the paw withdrawal latency (PWL). If no reaction was exhibited within 15 s the procedure was terminated and animals were assigned this withdrawal time. Thus 15 s effectively represents no withdrawal. A withdrawal response was often accompanied with repeated flinching or licking of the paw. Dynamic allodynia was considered to be present if animals responded to the cotton stimulus before 8 s of stroking.

Results

Effect of Gabapentin and Sildenafil Alone on CCI-Induced Static and Dynamic Allodynia Gabapentin dose-dependently (10-100 mg/kg, p.o.) blocked the maintenance of both static and dynamic allodynia with a minimum effective dose (MED) of 10 mg/kg (FIGS. 1, 2). The dose of 100 mg/kg produced a complete blockade of these responses. Sildenafil dose-dependently (10-30 mg/kg s.c.) blocked the maintenance of static allodynia with a minimum effective dose of 10 mg/kg and the dose of 30 mg/kg producing an approximate 60% blockade (FIG. 1). Sildenafil had a modest effect on the maintenance of dynamic allodynia with an MED of 30 mg/kg producing a 25% blockade (FIG. 2).

Effect of Combinations of Gabapentin and Sildenafil on CCI-Induced Static Allodynia Gabapentin and sildenafil had peak antiallodynic actions at 2 h post administration in the CCI-induced static model. Thus, for clarity all combination data are expressed at this time point. Gabapentin and sildenafil were administered at fixed dose ratios of 1:10, 1:1, 10:1 and 20:1. Following fixed dose ratios of 1:10 and 20:1, combinations of gabapentin and sildenafil produced an additive interaction (FIG. 3). However, the fixed dose ratio of 1:1 and 10:1 demonstrated synergy with static allodynia completely blocked by a total dose of 20 mg/kg and 11 mg/kg respectively (FIG. 3). The 1:1 combination represents a 10-fold lower dose of gabapentin and 3-fold lower dose of sildenafil when administered alone whilst the 1:1 ratio represents a 10-fold lower dose of gabapentin and 30-fold lower dose of sildenafil when administered alone.

Effect of Combinations of Gabapentin and Sildenafil on CCI-Induced Dynamic Allodynia Gabapentin and sildenafil had peak antiallodynic actions at 2 h post administration in the CCI-induced dynamic model. Thus, for clarity all combination data are expressed at this time point. Gabapentin and sildenafil were administered at fixed dose ratios of 1:10, 1:1, 10:1 and 20:1. Similar data were seen on dynamic allodynia to those with static allodynia. Following fixed dose ratios of 1:10 and 20:1, combinations of gabapentin and sildenafil produced an additive interaction (FIG. 4). However, the fixed dose ratio of 1:1 and 10:1 demonstrated synergy with static allodynia completely blocked by a total dose of 20 mg/kg and 1 1mg/kg respectively. The 1:1 combination represents a 10-fold lower dose of gabapentin and 3-fold lower dose of sildenafil when administered alone whilst the 1:1 ratio represents a 10-fold lower dose of gabapentin and 30-fold lower dose of sildenafil when administered alone.

Similar experiments were also performed in the same model for a further alpha-2-delta ligand (pregabalin) in combination with sildenafil and also with gabapentin and a further PDEV inhibitor, 3-Ethyl-5-[5-(4-ethyl-piperazine-1-sulfonyl)-2-propoxy-phenyl]-2-pyridin-2-ylmethyl-2,6-dihydropyrazolo[4,3-d]pyrimidin-7-one (Compound AA). The results for these experiments are summarized below and in tabular form (table 1 & 2).

TABLE 1

| Ratio Pregabalin:sildenafil | Pregabalin (mg/kg) | Sildenafil (mg/kg) | % reversal of allodynia | Total dose | Interaction |
|---|---|---|---|---|---|
| 1:0 | 30 | — | 100 | 30 | — |
| 0:1 | — | 30 | 50 | 30 | — |
| 1:1 | 10 | 10 | 100 | 20 | Synergy |
| 10:1 | 10 | 1 | 100 | 11 | Synergy |

TABLE 2

| Ratio Gabapentin: Compound AA | Gabapentin (mg/kg) | Sildenafil (mg/kg) | % reversal of allodynia | Total dose | Interaction |
|---|---|---|---|---|---|
| 1:0 | 100 | — | 100 | 100 | — |
| 0:1 | — | 30 | 50 | 30 | — |
| 10:1 | 10 | 1 | 100 | 11 | Synergy |

Effect of Combinations of Pregabalin and Sildenafil on CCI-Induced Static Allodynia.

Pregabalin and sildenafil had peak antiallodynic actions at 2 h post administration in the CCI-induced static model. Pregabalin and sildenafil were administered at fixed dose ratios of 1:1 and 10:1. These fixed dose ratios demonstrated synergy with static allodynia completely blocked by a total dose of 20 mg/kg and 11 mg/kg respectively. The 1:1 combination represents a 3-fold lower dose of pregabalin and 3-fold lower dose of sildenafil when administered alone whilst the 1:1 ratio represents a 3-fold lower dose of pregabalin and 30-fold lower dose of sildenafil when administered alone.

Effect of Combinations of Gabapentin and Compound AA on CCI-Induced Static Allodynia Gabapentin and Compound AA had peak antiallodynic actions at 2 h post administration in the CCI-induced static model. Gabapentin and Compound AA were administered at fixed dose ratios of 10:1. This fixed dose ratio demonstrated synergy with static allodynia completely blocked by a total dose of 11 mg/kg respectively. The the 1:1 ratio represents a 10-fold lower dose of gabapentin and 30-fold lower dose of Compound AA when administered alone.

Suitable PDEV inhibitors of the present invention may be prepared as described in the aforementioned patent literature references or are obvious to those skilled in the art on the basis of these documents.

Suitable alpha-2-delta ligand compounds of the present invention may be prepared as described herein below or in the aforementioned patent literature references or are obvious to those skilled in the art on the basis of these documents.

CHEMISTRY EXAMPLES

Example 1

(3S,5R)-3-Amino-5-methyl-octanoic acid hydrochloride(R)-2,6-Dimethyl-non-2-ene.

To (S)-citronellyl bromide (50 g, 0.228 mol) in THF (800 mL) at 0° C. was added LiCl (4.3 g) followed by CuCl$_2$ (6.8 g). After 30 minutes methylmagnesium chloride (152 mL of a 3 M solution in THF, Aldrich) was added and the solution warmed to room temperature. After 10 hours the solution was cooled to 0° C. and a saturated aqueous solution of ammonium chloride carefully added. The resultant two layers were separated and the aqueous phase extracted with ether. The combined organic phases were dried (MgSO$_4$) and concentrated to give (R)-2,6-dimethyl-non-2-ene. 32.6 g; 93%. Used without further purification. $^1$H NMR(400 MHz; CDCl$_3$) δ 5.1 (m, 1H), 1.95 (m, 2H), 1.62 (s, 3H), 1.6 (s, 3H), 1.3 (m, 4H), 1.2 (m, 2H), 0.8 (s, 6H); $^{13}$C NMR (100 MHz; CDCl$_3$) ⨅131.13, 125.28, 39.50, 37.35, 32.35, 25.92, 25.77, 20.31, 19.74, 17.81, 14.60.

(R)-4-Methyl-heptanoic acid. To (R)-2,6-dimethyl-non-2-ene (20 g, 0.13 mol) in acetone (433 mL) was added a solution of CrO$_3$ (39 g, 0.39 mol) in H$_2$SO$_4$ (33 mL)/H$_2$O (146 mL) over 50 minutes. After 6 hours a further amount of CrO$_3$ (26 g, 0.26 mol) in H$_2$SO$_4$ (22 mL)/H$_2$O (100 mL) was added. After 12 hours the solution was diluted with brine and the solution extracted with ether. The combined organic phases were dried (MgSO$_4$) and concentrated. Flash chromatography (gradient of 6:1 to 2:1 hexane/EtOAc) gave (R)-4-methyl-heptanoic acid as an oil. 12.1 g; 65%. MS, m/z (relative intensity): 143 [M−H, 100%].

(4R,5S)-4-Methyl-3-((R)-4-methyl-heptanoyl)-5-phenyl-oxazolidin-2-one. To (R)-4-methyl-heptanoic acid (19 g, 0.132 mol) and triethylamine (49.9 g, 0.494 mol) in THF (500 mL) at 0° C. was added trimethylacetylchloride (20 g, 0.17 mol). After 1 hour LiCl (7.1 g, 0.17 mol) was added followed by (4R,5S)-(+)-4-methyl-5-phenyl-2-oxazolidinone) 3 (30 g, 0.17 mol). The mixture was warmed to room temperature and after 16 hours the filtrate was removed by filtration and the solution concentrated under reduced pressure. Flash chromatography (7:1 hexane/EtOAc) gave (4R,5S)-4-methyl-3-((R)-4-methyl-heptanoyl)-5-phenyl-oxazolidin-2-one as an oil. 31.5 g; 79%. [a]$_D$=+5.5 (c 1 in CHCl$_3$). MS, m/z (relative intensity): 304 [M+H, 100%].

(3S,5R)-5-Methyl-3-((4R,5S)-4-methyl-2-oxo-5-phenyl-oxazolidine-3-carbonyl)-octanoic acid tert-butyl ester. To (4R,5S)-4-methyl-3-((R)-4-methyl-heptanoyl)-5-phenyl-oxazolidin-2-one (12.1 g, 0.04 mol) in THF (200 ml) at −50° C. was added sodium bis(trimethylsilyl)amide (48 mL of a 1 M solution in THF). After 30 min t-butylbromoaceate (15.6 g, 0.08 mol) was added. The solution was stirred for 4 hours at −50° C. and then warmed to room temperature. After 16 hours a saturated aqueous solution of ammonium chloride was added and the two layers separated. The aqueous phase was extracted with ether and the combined organic phases dried (MgSO$_4$) and concentrated. Flash chromatography (9:1 hexane/EtOAc) gave (3S,5R)-5-methyl-3-((4R,5S)-4-methyl-2-oxo-5-phenyl-oxazolidine-3-carbonyl)-octanoic acid tert-butyl ester as a white solid 12 g; 72%. [a]$_D$=+30.2 (c 1 in CHCl$_3$). $^{13}$C NMR (100 MHz; CDCl$_3$) δ176.47, 171.24, 152.72, 133.63, 128.87, 125.86, 80.85, 78.88, 55.34, 39.98, 38.77, 38.15, 37.58, 30.60, 28.23, 20.38, 20.13, 14.50, 14.28.

(S)-2-((R)-2-Methyl-pentyl)-succinic acid 4-tert-butyl ester. To (3S,5R)-5-methyl-3-((4R,5S)-4-methyl-2-oxo-5-phenyl-oxazolidine-3-carbonyl)-octanoic acid tert-butyl ester (10.8 g, 0.025 mol) in H$_2$O (73 mL) and THF (244 mL) at 0° C. was added a premixed solution of LiOH (51.2 mL of a 0.8 M solution) and H$_2$O$_2$ (14.6 mL of a 30% solution). After 4 hours a further 12.8 mL LiOH (0.8 M solution) and 3.65 mL of H$_2$O$_2$ (30% solution) was added. After 30 minutes sodium bisulfite (7 g), sodium sulfite (13 g), and water (60 mL) was added followed by hexane (100 mL) and ether (100 mL). The two layers were separated and the aqueous layer extracted with ether. The combined organic phases were concentrated to an oil that was dissolved in heptane (300 mL). The resultant solid was filtered off and the filtrate dried (MgSO$_4$) and concentrated to afford (S)-2-((R)-2-methyl-pentyl)-succinic acid 4-tert-butyl ester (6 g, 93%) which was used immediately without further purification. MS, m/z (relative intensity): 257 [M+H, 100%].

(3S, 5R)-3-Benzyoxycarbonylamino-5-methyl-octanoic acid, tert-butyl ester. A solution of (S)-2-((R)-2-methyl-pentyl)-succinic acid 4-tert-butyl ester (6.0 g, 23.22 mmol) and triethylamine (3.64 mL, 26.19 mmol) in toluene (200 mL) was treated with diphenylphosphoryl azide (5.0 mL, 23.22 mL) and stirred at room temperature for 0.5 hours. After the reaction mixture was then heated at reflux for 3 h and cooled briefly, benzyl alcohol was added (7.2 mL, 69.7 mmol) and the solution heated for another 3 h. After the reaction mixture was allowed to cool, it was diluted with ethyl ether (200 mL)

and the combined organic layer was washed successively with saturated NaHCO$_3$ and brine and dried (Na$_2$SO$_4$). The concentrated organic component was purified by chromatography (MPLC) eluting with 8:1 hexanes: ethyl acetate to provide (3S, 5R)-3-benzyoxycarbonylamino-5-methyl-octanoic acid, tert-butyl ester (6.4 g, 75.8%). MS: M+1: 364.2, 308.2.

(3S, 5R)-3-Amino-5-methyl-octanoic acid, tert-butyl ester. A solution of (3S, 5R)-3-benzyoxycarbonylamino-5-methyl-octanoic acid, tert-butyl ester (2.14 g, 5.88 mmol) in THF (50 mL) was treated with Pd/C (0.2 g) and H$_2$ at 50 psi for 2 hours. The reaction mixture was then filtered and concentrated to an oil in vacuo to give (3S, 5R)-3-amino-5-methyl-octanoic acid, tert-butyl ester in quantitative yield. MS: M+1: 230.2, 174.1.

(3S, 5R)-3-Amino-5-methyl-octanoic acid hydrochloride. A slurry of (3S, 5R)-amino-5-methyl-octanoic acid, tert-butyl ester (2.59 g, 11.3 mmol) in 6N HCl (100 mL) was heated under reflux 18 hours, cooled, and filtered over Celite. The filtrate was concentrated in vacuo to 25 mL and the resulting crystals were collected and dried to provide (3S, 5R)-3-amino-5-methyl-octanoic acid hydrochloride, mp 142.5–142.7° C. (1.2 g, 50.56%). A second crop (0.91 g) was obtained from the filtrate. Anal. Calc'd for C$_9$H$_{19}$NO$_2$.HCl: C, 51.55; H 9.61; N, 6.68; Cl, 16.91. Found: C: 51.69; H, 9.72; N, 6.56; Cl, 16.63.

(3S, 5R)-3-Amino-5-methyl-octanoic acid hydrochloride acid salt. 5.3 g of 2S-(2R-methyl-pentyl)-succinic acid-4-tert-butyl ester contained in 30 mL methyltertbutyl ether is reacted at room temperature with 3.5 mL triethylamine followed by 6.4 g of diphenylphosphoryl azide. After allowing the reaction to exotherm to 45° C. and stirring for at least 4 hours, the reaction mixture is allowed to cool to room temperature and stand while the phases separated. The lower layer is discarded and the upper layer is washed with water, followed by dilute aqueous HCl. The upper layer is then combined with 10 mL of 6 N aqueous HCl, and stirred at 45-65° C. The reaction mixture is concentrated by vacuum distillation to about 10-14 mL and allowed to crystallize while cooling to about 5° C. After collecting the product by filtration, the product is washed with toluene and reslurried in toluene. The product is dried by heating under vacuum resulting in 2.9 g (67%) of white crystalline product. The product may be recrystallized from aqueous HCl. mp 137° C., HNMR (400 MHz, D6 DMSO) δ 0.84-0.88 (overlapping d and t, 6H), 1.03-1.13 (m, 1H), 1.16-1.37 (m,4H), 1.57-1.68 (m, 2H), 2.55 (dd, 1H, J=7, 17 Hz), 2.67 (dd, 1H, J=6, 17 Hz), 3.40 (m, 1H), 8.1 (br s, 3H), 12.8 (br s, 1H).

Example 2

(3S, 5R)-Amino-5-methyl-heptanoic acid

Methanesulfonic acid (S)-3,7-dimethyl-oct-6-enyl ester. To S-(−)-citronellol (42.8 g, 0.274 mol) and triethylamine (91 mL, 0.657 mol) in CH$_2$CH$_2$ (800 mL) at 0° C. was added methanesulphonyl chloride (26 mL, 0.329 mol) in CH$_2$CH$_2$ (200 mL). After 2 hours at 0° C. the solution was washed with 1N HCl then brine. The organic phase was dried (MgSO$_4$) and concentrated to afford the titled compound an oil (60.5 g, 94%) which was used without further purification. MS, m/z (relative intensity): 139 [100%], 143 [100%].

(R)-2,6-Dimethyl-oct-2-ene. To methanesulfonic acid (S)-3,7-dimethyl-oct-6-enyl ester (60 g, 0.256 mol) in THF (1 L) at 0° C. was added lithium aluminum hydride (3.8 g, 0.128 mol). After 7 hours, a further 3.8 g of lithium aluminum hydride was added and the solution warmed to room temperature. After 18 hours, a further 3.8 g of lithium aluminum hydride was added. After a further 21 hours, the reaction was carefully quenched with 1N citric acid and the solution diluted further with brine. The resultant two phases were separated and the organic phase was dried (MgSO$_4$) and concentrated to afford the titled compound as an oil which was used without further purification. MS, m/z (relative intensity): 139 [M+H, 100%].

(R)-4-Methyl-hexanoic acid. A procedure similar to the synthesis of (R)-4-methyl-heptanoic acid was utilized giving the acid as an oil (9.3 g, 56%). IR (film) 2963, 2931, 2877, 2675, 1107, 1461, 1414 cm$^{-1}$; MS, m/z (relative intensity): 129 [M–H, 100%].

(4R,5S)-4-Methyl-3-((R)-4-methyl-hexanoyl)-5-phenyl-oxazolidin-2-one. A procedure similar to the synthesis of (4R,5S)-4-methyl-3-((R)-4-methyl-heptanoyl)-5-phenyl-oxazolidin-2-one was utilized giving the titled compound as an oil (35.7 g, 95%). MS, m/z (relative intensity): 290 [M+H, 100.

(3S,5R)-5-Methyl-3-[1-((4R,5S)-4-methyl-2-oxo-5-phenyl-oxazolidin-3-yl)-methanoyl]-heptanoic acid tert-butyl ester. A procedure similar to the preparation of (3S,5R)-5-methyl-3-((4R,5S)-4-methyl-2-oxo-5-phenyl-oxazolidine-3-carbonyl)-octanoic acid tert-butyl ester was followed giving the titled compound as an oil (7.48 g; 31%). MS, m/z (relative intensity): 178 [100%], 169 [100%]; [α]$_D$=+21.6 (c 1 in CHCl$_3$).

(S)-2-((R)-2-Methyl-butyl)-succinic acid 4-tert-butyl ester. (3S,5R)-5-Methyl-3-[1-((4R,5S)-4-methyl-2-oxo-5-phenyl-oxazolidin-3-yl)-methanoyl]-heptanoic acid tert-butyl ester (7.26 g, 0.018 mol) in H$_2$O (53 mL) and THF (176 mL) at 0° C. was added a premixed solution of LiOH (37 mL of a 0.8 M solution) and H$_2$O$_2$ (10.57 mL of a 30% solution) and the solution warmed to room temperature. After 2 hours sodium bisulfite (7 g), sodium sulfite (13 g), and water (60 mL) was added and the two layers were separated and the aqueous layer extracted with ether. The combined organic phases were concentrated to an oil that was dissolved in heptane (200 mL). The resultant solid was filtered off and the filtrate dried (MgSO$_4$) and concentrated to afford the titled compound as an oil (4.4 g) that was used without further purification. MS, m/z (relative intensity): 243 [100%].

(3S, 5R)-3-Benzyoxycarbonylamino-5-methyl-heptanoic acid, tert-butyl ester—This compound was prepared as described above starting with (S)-2-((R)-2-methyl-butyl) succinic acid, 4-tert-butyl ester to give (3S, 5R)-3-benzyoxycarbonylamino-5-methyl-heptanoic acid, tert-butyl ester as an oil (73.3% yield). $^1$H NMR(400 MHz; CDCl$_3$) δ 0.84(t, 3H, J=7.33 Hz), 0.89(d, 3H, J=6.60 Hz), 1.12-1.38 (m, 4H), 1.41 (s, 9H), 1.43-1.59 (m, 2H), 2.42 (m, 2H), 4.05 (m, 1H), 5.07 (t, 2H J=12.95 Hz), and 7.28-7.34 (m, 5H).

(3S, 5R)-Amino-5-methyl-heptanoic acid, tert-butyl ester—This compound was prepared as described above starting with (3S, 5R)-3-benzyoxycarbonylamino-5-methyl-heptanoic acid, tert-butyl ester instead of (3S, 5R)-3-benzyoxycarbonylamino-5-methyl-octanoic acid, tert-butyl ester to give the titled compound. $^1$H NMR(400 MHz; CDCl$_3$) δ 0.84 (overlapping t and d, 6H), 1.08-1.16(m, 2H), 1.27-1.30 (m, 2H), 1.42(s, 9H), 1.62 (br s, 2H), 2.15 (dd, 1H, J=8.54 and 15.62 Hz), 2.29(dd, 1H, J=4.15 and 15.37 Hz), and 3.20(br s, 2H).

(3S, 5R)-Amino-5-methyl-heptanoic acid hydrochloride—A slurry of (3S, 5R)-amino-5-methyl-heptanoic acid, tert-butyl ester (1.44 g, 6.69 mmol) in 3N HCl was heated at reflux for 3 hours, filtered hot over Celite, and concentrated to dryness. Trituration of the resulting solid in ethyl ether provided (3S, 5R)-3-amino-5-methyl-heptanoic acid hydrochloride, (0.95 g, 85%) mp 126.3-128.3° C. Anal. Calc'd for C$_8$H$_{17}$NO$_2$.HCl.0.1H$_2$O: C, 48.65; H, 9.29; N, 7.09; Cl, 17.95. Found: C: 48.61; H, 9.10; N, 7.27; Cl, 17.87 MS: M+1: 160.2

Example 3

(3S, 5R)-3-Amino-5-methyl-nonanoic acid (R)-4-Methyl-octanoic acid. Lithium chloride (0.39 g, 9.12 mmol) and copper (I) chloride (0.61 g, 4.56 mmol) were combined in 45 ml THF at ambient temperature and stirred 15 minutes, then cooled to 0° C. at which time ethylmagnesium bromide (1 M solution in THF, 45 mL, 45 mmol) was added. (S)-citronellyl bromide (5.0 g, 22.8 mmol) was added dropwise and the solution was allowed to warm slowly to ambient temperature with stirring overnight. The reaction was quenched by cautious addition of sat. NH$_4$Cl (aq), and stirred with Et$_2$O and sat. NH$_4$Cl (aq) for 30 minutes. The phases were separated and the organic phase dried (MgSO$_4$) and concentrated. The crude (R)-2,6-dimethyl-dec-2-ene was used without purification. To a solution of (R)-2,6-dimethyl-dec-2-ene (3.8 g, 22.8 mmol) in 50 mL acetone at 0° C. was added Jones'0 reagent (2.7 M in H$_2$SO$_4$ (aq), 40 mL, 108 mmol) and the solution was allowed to warm slowly to ambient temperature with stirring overnight. The mixture was partitioned between Et$_2$O and H$_2$O, the phases were separated, and the organic phase washed with brine, dried (MgSO$_4$), and concentrated. The residue was purified by flash chromatography (8:1 hexanes:EtOAc) to afford 2.14 g (59%) of the titled compound as a colorless oil: LRMS: m/z 156.9 (M+). Jones' reagent was prepared as a 2.7M solution by combining 26.7 g CrO$_3$, 23 mL H$_2$SO$_4$, and diluting to 100 mL with H$_2$O.

(4R, 5S)-4-Methyl-3-((R)-4-methyl-octanoyl)-5-phenyl-oxazolidin-2-one. To (R)-4-methyl-octanoic acid (2.14 g, 13.5 mmol) in 25 mL CH$_2$Cl$_2$ at 0° C. was added 3 drops DMF, followed by oxalyl chloride (1.42 mL, 16.2 mmol) resulting in vigorous gas evolution. The solution was warmed directly to ambient temperature, stirred 30 minutes, and concentrated. Meanwhile, to a solution of the oxazolidinone (2.64 g, 14.9 mmol) in 40 mL THF at −78° C. was added n-butyllithium (1.6 M soln in hexanes, 9.3 mL, 14.9 mmol) dropwise. The mixture was stirred for 10 minutes at which time the acid chloride in 10 mL THF was added dropwise. The reaction was stirred 30 minutes at −78° C., then warmed directly to ambient temperature and quenched with sat. NH$_4$Cl. The mixture was partitioned between Et$_2$O and sat. NH$_4$Cl (aq), the phases were separated, and the organic phase dried (MgSO$_4$), and concentrated to furnish 3.2 g of the titled compound as a colorless oil. LRMS: m/z 318.2 (M+).

(3S,5R)-5-Methyl-3-((4R,5S)-4-methyl-2-oxo-5-phenyl-oxazolidine-3-carbonyl)-nonanoic acid tert-butyl ester. To a solution of diisopropylamine (1.8 mL, 12.6 mmol) in 30 mL THF at −78° C. was added n-butyllithium (1.6 M soln in hexanes, 7.6 mL, 12.1 mmol), and the mixture stirred 10 minutes at which time (4R, 5S)-4-Methyl-3-((R)-4-methyl-octanoyl)-5-phenyl-oxazolidin-2-one (3.2 g, 10.1 mmol) in 10 mL THF was added dropwise. The solution was stirred for 30 minutes, t-butyl bromoacetate (1.8 mL, 12.1 mmol) was added quickly dropwise at −50° C., and the mixture was allowed to warm slowly to 10° C. over 3 hours. The mixture was partitioned between Et$_2$O and sat. NH$_4$Cl (aq), the phases were separated, and the organic phase dried (MgSO$_4$), and concentrated. The residue was purified by flash chromatography (16:1 to 8:1 hexanes:EtOAc) to provide 2.65 g (61%) of the titled compound as a colorless crystalline solid, mp=84-86° C. [δ]$_D^{23}$+17.1 (c=1.00, CHCl$_3$).

(S)-2-((R)-2-Methyl-hexyl)-succinic acid 4-tert-butyl ester. To a solution of (3S,5R)-5-Methyl-3-((4R,5S)-4-methyl-2-oxo-5-phenyl-oxazolidine-3-carbonyl)-nonanoic acid tert-butyl ester (2.65 g, 6.14 mmol) in 20 mL THF at 0° C. was added a precooled (0° C.) solution of LiOH monohydrate (1.0 g, 23.8 mmol) and hydrogen peroxide (30 wt % aqueous soln, 5.0 mL) in 10 mL H$_2$O. The mixture was stirred vigorously for 90 minutes, then warmed to ambient temperature and stirred 90 minutes. The reaction was quenched at 0° C. by addition of 100 mL 10% NaHSO$_3$ (aq), then extracted with Et$_2$O. The phases were separated, and the organic phase washed with brine, dried (MgSO$_4$), and concentrated. The titled compound was used without purification.

(3S, 5R)-3-Benzyoxycarbonylamino-5-methylnonanoic acid, tert-butyl ester—This compound was prepared similarly as described above starting with (S)-2-((R)-2-methylhexyl) succinic acid, 4-tert-butyl ester instead of (S)-2-((R)-2-methylpentyl) succinic acid, 4-tert-butyl ester to provide the titled compound as an oil (71.6% yield). $^1$HNMR(400 MHz; CDCl$_3$) δ 0.81(t, 3H, J=4.40 Hz), 0.85(d, 3H, J=6.55 Hz), 1.06-1.20(m, 7H), 1.36(s, 9H), 1.38-1.50(m, 2H), 2.36(m, 2H), 3.99(m, 1H), 5.02(m+s, 3H), and 7.28-7.28(m, 5H).

(3S, 5R)-3-Amino-5-methyl-nonanoic acid, tert-butyl ester—This compound was prepared as described above starting with (3S, 5R)-benzyoxycarbonylamino-5-methyl-nonanoic acid, tert-butyl ester instead of (3S, 5R)-3-benzyoxycarbonylamino-5-methyl-octanoic acid, tert-butyl ester. Yield=97%. $^1$HNMR(400 MHz; CDCl$_3$) δ 0.82(overlapping d and t, 6H), 1.02-1.08(m, 1H), 1.09-1.36(m, 6H), 1.39(s, 9H), 1.47(br s, 1H), 1.80(s, 2H), 2.13(dd, 1H, J=8.54 and 15.61 Hz), and 2.27(dd, 1H, J=4.15 and 15.38 Hz).

(3S, 5R)-3-Amino-5-methyl-nonanoic acid hydrochloride—A mixture of (3S, 5R)-3-amino-5-methyl-nonanoic acid, tert-butyl ester (1.50 g, 6.16 mmol) in 3N HCl (100 mL) was heated at reflux for 3 hours, filtered hot over Celite, and concentrated to 30 mL in vacuo. The resulting crystals were collected, washed with additional 3N HCl, and dried to provide the title compound, mp 142.5-143.3° C. Additional crops were obtained from the filtrate to provide 1.03 g (70.4%). Anal. Calc'd for C$_{10}$H$_{21}$NO$_2$.HCl: C: 53.68; H, 9.91; N, 6.26; Cl: 15.85. Found: C: 53.89; H, 10.11; N, 6.13. MS: M+1: 188.1.

Example 4

(2R, 4R)-2-Aminomethyl-4-methyl-heptanoic acid

5R-Methyl-3R-(4S-methyl-2-oxo-5R-phenyloxazolidine-3-carbonyl)octanoic acid. A solution of (3R,5R)-5-Methyl-3-((4S,5R)-4-methyl-2-oxo-5-phenyl-oxazolidine-3-carbonyl)-octanoic acid tert-butyl ester(3.9 g, 9.34 mmol) in dichloromethane (150 mL) was treated with trifluoroacetic acid (7.21 mL, 93.4 mL) and stirred 18 hours at ambient temperature. After the solvents and reagent were removed in vacuo, the resulting residue was triturated in 100 hexanes to provide 3.38 g of the title compound (100%) mp 142-143° C.

[4R-Methyl-2R-(4S-methyl-2-oxo-5R-phenyloxazolidine-3-carbonyl)heptyl]carbamic acid benzyl ester. A solution of 5R-methyl-3R-(4S-methyl-2-oxo-5R-phenyloxazolidine-3-carbonyl)octanoic acid (1.98 g, 5.48 mmol) and triethylamine (0.92 mL, 6.57 mmol) was treated with diphenylphosphorylazide (1.2 mL, 5.48 mmol), stirred 30 min at ambient temperature and then heated at reflux for 3 hours. After cooling briefly, the reaction mixture was treated with benzyl alcohol (2.8 mL, 27.4 mmol) and heated for an additional 3 h at reflux. The reaction mixture was cooled, diluted with ethyl ether (150 mL), washed successively with sat'd NaHCO$_3$ and brine, dried (MgSO$_4$) and concentrated in vacuo to an oil. Chromatography (MPLC, elution with 4:1 hexanes:ethyl acetate) provided the title compound (2.0 g, 78.3%) as an oil. MS M+1=467.1.

2R-(Benzyloxycarbonylaminomethyl)-4R-methylheptanoic acid. A solution of 4R-methyl-2R-(4S-methyl-2-oxo-5R-phenyloxazolidine-3-carbonyl)heptyl]carbamic acid benzyl ester (4.12 g, 8.83 mmol) in 3:1 THF:water (100 mL) was cooled to 0° C. and treated with a mixture of 0.8 N LiOH (17.5 mL, 14 mmol) and 30% H$_2$O$_2$ (4.94 mL, 44 mmol). After the reaction mixture was stirred in the cold 3 hours, it was quenched with a slurry of NaHSO$_3$ (2.37 g) and Na$_2$SO$_3$ (4.53 g) in water (30 mL) and stirred 1 hour. The reaction mixture was diluted with ethyl ether (200 mL), partitioned, and the organic layer washed with brine and dried (MgSO$_4$). The concentrated organic extract was chromatographed (MPLC) eluting with ethyl acetate to give 1.25 g of 2R-(benzyloxycarbonylaminomethyl)-4R-methylheptanoic acid (46%). MS M+1=308.1.

(2R,4R)-2-Amino-4-methyl-heptanoic acid hydrochloride. A mixture of 2R-(benzyloxycarbonylaminomethyl)-4R-methyl-heptanoic acid (1.25 g, 4.07 mmol) and Pd/C (20%, 0.11 g) in methanol (50 mL) was hydrogenated at 50 psi for 18 hours. After the catalyst was removed by filtration, the solvent was removed in vacuo and the resulting solid triturated in ether to provide (2S, 4R)-2-amino-4-methyl-heptanoic acid hydrochloride (0.28 g, 40%) mp 226.3-228.0° C. MS M+1=174.0. Anal. Calc'd for C$_9$H$_{19}$NO$_2$.0.1 H$_2$O C, 61.75; H, 11.06; N, 8.00. Found C: 61.85; H, 10.83; N, 8.01.

Example 5

2-Aminomethyl-4,4-dimethyl-heptanoic acid hydrochloride

2-Cyano-4,4-dimethyl-hepta-2,6-dienoic acid ethyl ester. A solution of 2,2-dimethyl-pent-4-enal (5.0 g, 44 mmol), cyano-acetic acid ethyl ester (5.12 mL, 48 mmol), piperidine (1.3 mL, 14 mmol) and acetic acid (4.52 mL, 80 mmol) in 170 mL of toluene was heated under reflux for 18 hours in a flask equipped with a Dean-Stark separator. Several mL of water was collected in the trap. The reaction was cooled and washed with 1N HCl, NaHCO$_3$ and brine, successively. The organic layers were dried over Na$_2$SO$_4$ and concentrated to an oil. This oil was chromatographed eluting with 20% of EtOAc in hexane to give a combination of two lots total 8.3 g (91%). $^1$H NMR (400 MHz; CDCl$_3$) 1.28 (s, 6H), 1.32 (t, 3H, J=7 Hz), 2.26 (d, 2H, J=7.6 Hz), 4.27 (q, 2H, J=7.2 Hz), 5.08 (d, 1H, J=12 Hz), 5.10 (d, 1H, J=4 Hz), 5.72 (m, 1H).

2-Aminomethyl-4,4-dimethyl-heptanoic acid hydrochloride. 2-Cyano-4,4-dimethyl-hepta-2,6-dienoic acid ethyl ester (5.88 g, 28 mmol) was dissolved in the mixture of 91 mL of ethanol and 6 mL of HCl and treated with 0.4 g of PtO$_2$. The reaction was carried out under 100 psi of hydrogen pressure at room temperature for 15 hours. The catalyst was filtered and filtrate was concentrated to give 3.8 g of the desired product 2-aminomethyl-4,4-dimethyl-heptanoic acid ethyl ester as an oil. MS (APCI): 216.2 (M+1)$^+$. This oil was refluxed in 75 mL of 6N HCl for 18 hours. While the reaction was cooled, a precipitate formed. The solid was filtered, washed with additional HCl solution and triturated with ether to give the clean title compound. MS (APCI): 188.1 (M+1)$^+$. 186.1 (M−1)$^+$. $^1$H NMR(400 MHz; CD$_3$OD): 0.91 (9H, m), 1.30 (5H, m), 1.81 (dd, 1H, J=7.2 Hz, 14.4 Hz), 2.72 (1H, m), 3.04 (2H, m); Anal. Calc'd for C$_{10}$H$_{21}$NO$_2$.HCl: C: 53.68; H, 9.91; N, 6.26; Cl: 15.85. Found: C: 53.83; H, 10.15; N, 6.22; Cl: 15.40. MP: 229.5-231.0° C.

Example 6

(S)-3-Amino-5,5-dimethyl-octanoic acid 3-(4,4-Dimethyl-heptanoyl)-(R)-4-methyl-(S)-5-phenyl-oxazolidin-2-one: A solution of 4,4-dimethyl-heptanoic acid (1.58 g, 10 mmol) and triethylamine (4.6 mL) in 50 mL THF was cooled to 0° C. and treated with 2,2-dimethyl-propionyl chloride (1.36 mL). After one hour, 4R-methyl-5S-phenyl-oxazolidin-2-one (1.95 g, 11 mmol) and lithium chloride (0.47 g, 11 mmol)was added and the mixture was stirred for 18 hours. The precipitate was filtered and washed thoroughly with additional THF. The filtrate was concentrated in vacuo to give an oily solid. This solid was dissolved in 200 mL Et$_2$O, washed successively with saturated NaHCO$_3$, 0.5N HCl and saturated NaCl, dried (MgSO$_4$) and concentrated in vacuo to give the title compound as an oil (3.0 g, 95%). $^1$HNMR(400 MHz; CDCl$_3$): 0.73-0.84 (m, 12H), 1.10-1.22 (m, 4H), 1.46-1.54 (m, 2H), 2.75-2.87 (m, 2H), 4.70 (m, 1H, J=7 Hz), 5.59 (d, 1H, J=7 Hz), 7.22-7.37 (m, 5H).

5,5-Dimethyl-(S)-3-((R)-4-methyl-2-oxo-(S)-5-phenyl-oxazolidine-3-carbonyl)-octanoic acid tert-butyl ester: According to example 1, 5.07 g (16 mmol) of 3-(4,4-dimethyl-heptanoyl)-4-methyl-5-phenyl-oxazolidin-2-one, 18 mL (1N, 18 mmol) of NaHMDS solution and 4.72 mL (32 mmol) of bromo-acetic acid tert-butyl ester gave 3.40 g (49.3%) of the title compound as a crystalline solid. m.p.: 83-85° C.

(S)-2-(2,2-Dimethyl-pentyl)-succinic acid 4-tert-butyl ester: According to example 1, 3.4 g (7.9 mmol) of 5,5-dimethyl-3-(4-methyl-2-oxo-5-phenyl-oxazolidine-3-carbonyl)-octanoic acid tert-butyl ester, 16 mL (12.8 mmol) of 0.8N LiOH and 4.5 mL of 30% H$_2$O$_2$ gave 2.42 g (>100%) of the title compound as an oil. $^1$HNMR(400 MHz; CDCl$_3$): 0.77-0.82 (m, 9H), 1.14-1.29 (m, 5H), 1.42 (s, 9H), 1.77 (dd, 1H, J=8 Hz, 16 Hz), 2.36 (dd, 1H, J=6 Hz, 16 Hz), 2.59 (dd, 1H, J=8 Hz, 16 Hz), 2.75-2.85 (m, 1H).

(S)-3-Benzyloxycarbonylamino-5,5-dimethyl-octanoic acid tert-butyl ester: According to example 1, 2.14 g (7.9 mmol)of 2-(2,2-dimethyl-pentyl)-succinic acid 4-tert-butyl ester, 1.7 mL of DPPA, 1.1 mL of Et$_3$N and 2.44 mL of BnOH provided 1.63 g (54.8% in two steps) of the title compound as an oil. $^1$HNMR (400 MHz; CDCl$_3$): 0.78-0.89 (m, 9H), 1.10-1.30 (m, 5H), 1.36 (s, 9H), 2.39 (t, 2H, J=5 Hz), 4.95-4.05 (m, 1H), 5.00 (s, 2H), 5.09 (d, 1H, J=9.6 Hz), 7.22-7.30 (m, 5H).

(S)-3-Amino-5,5-dimethyl-octanoic acid tert-butyl ester: According to example 1, 1.63 g of 3-benzyloxycarbonylamino-5,5-dimethyl-octanoic acid tert-butyl ester and 0.2 g of 20% Pd/C furnished the title compound. MS, m/z, 244.2 (M+1)$^+$.

(S)-3-Amino-5,5-dimethyl-octanoic acid hydrochloride: According to example 1, 3-amino-5,5-dimethyl-octanoic acid tert-butyl ester was treated with 3N HCl to provide 286 mg of the title compound as a solid. MS (APCl), m/z: 188.1 (M+1)$^+$. 186.1 (M−1)$^+$. Anal. Calc'd for C$_{10}$H$_{21}$NO$_2$.HCl.0.12H$_2$O: C: 53.17; H, 9.92; N, 6.20; Cl: 15.69; Found: C: 53.19; H, 10.00; N, 6.08; Cl: 15.25. α=+20° (MeOH). MP: 194.2-195.2° C.

Example 7

2-Aminomethyl-3-(1-methyl-cyclopropyl)-propionic acid

2-Cyano-3-(1-methyl-cyclopropyl)-acrylic acid ethyl ester. To 1-methylcyclopropane-methanol (Aldrich, 1.13 mL, 11.6 mmol) in 50 mL $CH_2Cl_2$ was added neutral alumina (2.5 g) and then PCC (2.5 g, 11.6 mmol), and the mixture stirred 3 h at ambient temperature. The mixture was filtered through a 1 cm plug of silica gel under vacuum, and rinsed with $Et_2O$. The filtrate was concentrated to ca. 5 mL total volume. To the residue was added THF (10 mL), ethyl cyanoacetate (1.2 mL, 11.3 mmol), piperidine (5 drops), and finally acetic acid (5 drops). The whole was stirred at ambient temperature overnight, then partitioned between $Et_2O$ and sat. aq. $NaHCO_3$. The phases were separated and the organic phase washed with brine, dried ($MgSO_4$), and concentrated. Flash chromatography of the residue (10→15% EtOAc/hexanes) provided 0.53 g (25%) of the ester as a colorless oil that crystallized on standing. Anal. Calcd for $C_{10}H_{13}NO_2$: C, 67.02; H, 7.31; N, 7.82. Found: C, 66.86; H, 7.47; N, 7.70.

2-Aminomethyl-3-(1-methyl-cyclopropyl)-propionic acid ethyl ester. To 2-cyano-3-(1-methyl-cyclopropyl)-acrylic acid ethyl ester (0.45 g, 2.51 mmol) in 16 mL EtOH:THF (1:1) was added RaNi (0.4 g), and the mixture was hydrogenated in a Parr shaker at 48 psi for 15.5 h. Pearlman's catalyst (0.5 g) was then added and hydrogenation was continued for an additional 15 h. The mixture was filtered and concentrated. Flash chromatography of the residue 2→3→4→5→6→8% MeOH/$CH_2Cl_2$ provided 0.25 g (54%) of the aminoester as a colorless oil. LRMS: m/z 186.1 (M+1).

2-Aminomethyl-3-(1-methyl-cyclopropyl)-propionic acid. To a solution of 2-aminomethyl-3-(1-methyl-cyclopropyl)-propionic acid ethyl ester (0.25 g, 1.35 mmol) in 10 mL methanol at 0° C. was added 10% aq. NaOH (10 mL). The mixture was stirred at ambient temperature overnight, then concentrated to remove the methanol. The residue was cooled to 0° C. and acidified to pH 2 with conc. HCl. After allowing to warm to ambient temperature the mixture was loaded onto DOWEX-50WX8-100 ion exchange resin and eluted with $H_2O$ until neutral to litmus. Elution was continued with 5% aq. $NH_4OH$ (100 mL) and the alkaline fractions concentrated to provide 0.15 g (71%) of the amino acid as a colorless solid. LRMS: m/z 158.0 (M+1).

Example 8

(3S,5R)-3-Amino-5-methyl-octanoic acid (5S)-5-Methyl-octa-2,6-dienoic acid tert-butyl ester. To a solution of (S)-3-methyl-hex-4-enoic acid ethyl ester* (1.0 g, 6.4 mmol) in 30 mL toluene at −78° C. was added DIBAH (1.0 M in THF, 6.4 mL) dropwise over 5 min. The mixture was stirred at −78° C. 45 min at which time 5 drops of methanol were added, resulting in vigorous $H_2$ evolution. Methanol was added until no more gas evolution was observed (ca. 5 mL). At this time the cold bath was removed and ca. 5 mL of sat. aq. $Na^+K^+$ tartrate was added. When the mixture reached room temperature, additional sat. aq. $Na^+K^+$ tartrate and $Et_2O$ were added and stirring was continued until the phases were mostly clear (ca. 1 h). The phases were separated, and the organic phase washed with brine, dried ($MgSO_4$), and concentrated to ca. 10 mL total volume owing to volatility concerns. The crude mixture was combined with an additional batch of aldehyde prepared from 10 mmol of the ester by the method described above and the whole used without purification. To a suspension of sodium hydride (60% dispersion in mineral oil) in 25 mL THF was added t-butyl-P, P-dimethylphosphonoacetate (3.0 mL, 15 mmol) dropwise over 1 h such that the evolution of $H_2$ was under control. After the addition was complete, the crude aldehyde in toluene (ca. 20 mL total volume) was added quickly dropwise and the mixture stirred at ambient temperature overnight. The mixture was partitioned between $Et_2O$ and sat. aq. $NH_4Cl$, the phases separated, the organic phase washed with brine, dried ($MgSO_4$), and concentrated. Flash chromatography of the residue (0→3→5% EtOAc/hexanes) afforded 1.0 g (29%, two steps) of the unsaturated ester as a pale yellow oil: $^1H$ NMR($CDCl_3$) δ 6.75 (m, 1H), 5.66 (m, 1H), 5.30 (m, 2H), 2.03-2.29 (m, 3H), 1.58 (d, J=6.1 Hz, 3H), 1.41 (s, 9H), 0.91 (d, J=6.6 Hz, 3H).

*(S)-3-methyl-hex-4-enoic acid ethyl ester was prepared from (S)-trans-3-Penten-2-ol [Liang, J.; Hoard, D. W.; Van Khau, V.; Martinelli, M. J.; Moher, E. D.; Moore, R. E.; Tius, M. A. *J. Org. Chem.*, 1999, 64, 1459] via Johnson-Claisen rearrangement with triethylorthoacetate according to the literature protocol [Hill, R. K.; Soman, R.; Sawada, S., *J. Org. Chem.*, 1972, 37, 3737].

(3R,5S)-3-[Benzyl-(1-phenyl-ethyl)-amino]-5-methyl-oct-6-enoic acid tert-butyl ester. To a solution of (S)-(−)-N-benzyl-α-methylbenzylamine (0.60 mL, 2.85 mmol) in 9.0 mL THF at −78° C. was added n-butyllithium (1.6M in hexanes, 1.6 mL) quickly dropwise resulting in a deep pink color. The mixture was stirred at −78° C. for 30 min at which time (5S)-5-Methyl-octa-2,6-dienoic acid tert-butyl ester (0.5 g, 2.38 mmol) in 1.0 mL THF was added slowly dropwise, resulting in a pale tan color which darkened over 3 h. The mixture was stirred 3 h at −78° C., then quenched with sat. aq. $NH_4Cl$. The mixture was allowed to warm to rt and stirred overnight, then partitioned between EtOAc and sat. aq. $NH_4Cl$. The phases were concentrated, and the organic phase dried ($MgSO_4$), and concentrated. Flash chromatography of the residue (3→5% EtOAc/hexanes) provided 0.52 g (52%) of the aminoester as a yellow oil. $^1H$ NMR ($CDCl_3$) δ 7.34 (m, 2H), 7.20 (m, 8H), 5.27 (m, 2H), 3.74 (m, 1H), 3.72 (d, J=15.9 Hz, 1H), 3.41 (d, J=14.9 Hz, 1H), 3.27 (m, 1H), 2.38 (m, 1H), 1.98 (dd, J=3.7, 14.2 Hz, 1H), 1.81 (dd, J=9.3, 14.4 Hz, 1H), 1.54 (d, J=4.9 Hz, 3H), 1.32 (s, 9H), 1.24 (d, J=7.1 Hz, 3H), 0.99 (m, 2H), 0.74 (d, J=6.6 Hz, 3H).

(3S,5R)-3-Amino-5-methyl-octanoic acid. To a solution of (3R,5S)-3-[Benzyl-(1-phenyl-ethyl)-amino]-5-methyl-oct-6-enoic acid tert-butyl ester (0.92 g, 2.18 mmol) in 50 mL MeOH was added 20% Pd/C (0.20 g), and the mixture was hydrogenated in a Parr shaker at 48 psi for 23 h. The mixture was filtered and concentrated. To the crude aminoester in 10 mL $CH_2Cl_2$ was added 1.0 mL trifluoroacetic acid, and the solution stirred at ambient temperature overnight. The mixture was concentrated, and the residue dissolved in the minimum amount of $H_2O$, and loaded onto DOWEX-50WX8-100 ion exchange resin. The column was eluted with $H_2O$ until neutral to litmus, then continued with 5% aq. $NH_4OH$ (100 mL). The alkaline fractions were concentrated to provide 0.25 g (66%, two steps) of the amino acid as an off-white solid. $^1H$ NMR(CD3OD) δ 3.41 (m, 1H), 2.36 (dd, J=5.1, 16.6 Hz, 1H), 2.25 (dd, J=8.1, 16.6 Hz, 1H), 1.42 (m, 2H), 1.24 (m, 1H), 1.12 (m, 2H), 1.00 (m, 1H), 0.73 (d, J=6.4 Hz, 3H), 0.68 (t, J=6.8 Hz, 3H). LRMS: m/z 172.1 (M−1).

Example 9

2-Aminomethyl-8-methyl-nonanoic acid

A procedure similar to that of 2-Aminomethyl-4,4,8-trimethyl-nonanoic acid was utilized to prepare 2-Aminomethyl-8-methyl-nonanoic acid from 6-methyl-1-heptanol m/z 202.1 (M+).

2-Aminomethyl-4,8-dimethyl-nonanoic acid (R)-2,6-dimethyl heptan-1-ol: Magnesium turnings (2.04 g, 84 mmol) and a crystal of iodine were suspended in 5 mL THF for the addition of 1-bromo-3-methyl butane (0.3 mL, neat). The mixture was heated to start the Grignard formation.

The remaining 1-bromo-3-methyl butane (8.63 mL, 72 mmol) was diluted in THF (60 mL) and added dropwise. The mixture was stirred at ambient temperature for 2 hours and cooled to −5° C. A solution of copper chloride (1.21 g, 9 mmol) and LiCl (0.76 g, 18 mmol) in THF (50 mL) was added dropwise keeping the temperature below 0° C. The resulting mixture was stirred for 20 min, and (R)-3-bromo-2-methyl-propanol in THF (20 mL) was added dropwise while keeping the temperature below 0° C. The mixture was allowed to slowly reach ambient temperature overnight. The reaction mixture was quenched with ammonium hydroxide and water. The mixture was diluted with EtOAc and extracted with 3×20 mL EtOAc. The organics were washed with brine, dried ($MgSO_4$), filtered and concentrated. The residual oil was purified via silica gel chromatography (90/10 Hexane/EtOAc) to give 2.67 g (R)-2,6-dimethyl heptan-1-ol.

(R)-1-iodo-2,6-dimethyl heptane: To a mixture of supported triphenyl phosphine (6.55 g, 19.67 mmol) in $CH_2Cl_2$ at 0° C. was added iodine (4.99 g, 19.67 mmol) and imidazole (1.33 g, 19.67 mmol). The mixture was warmed to ambient temperature, stirred for 1 h and cooled to 0° C. for the dropwise addition of (R)-2,6-dimethyl heptan-1-ol in $CH_2Cl_2$ (5 mL). The mixture was allowed to reach ambient temperature and stirred for 1 h, at which time it was filtered through a pad of celite and the solids were washed with $CH_2Cl_2$. The filtrated was concentrated, and the crude product was purified via silica gel chromatography to give (R)-1-iodo-2,6-dimethyl heptane (2.44 g).

(4R)-4,8-dimethyl nonanoic acid t-butyl ester: To diisopropyl amine (0.827 mL, 5.9 mmol) in THF (8 mL) at −78° C. was added nBuLi (2.65 mL of a 2.6 M solution in pentane). The solution was stirred for 30 min at −78° C., followed by the addition of t-butyl acetate (0.8 mL, 5.9 mmol). The mixture was stirred at −78° C. for 2 h, and then (R)-1-iodo-2,6-dimethyl heptane (0.3 g, 1.18 mmol) and HMPA (1.5 mL) in THF (1 mL) was added. The reaction was stirred at −78° C. and allowed to slowly reach ambient temperature overnight, then heated at 35° C. to drive the reaction to completion. The reaction was quenched by the addition of ammonium chloride (saturated aqueous solution), and the mixture was extracted with EtOAc (2×10 mL). The organics were combined, washed with water, dried ($MgSO_4$), filtered and concentrated. Silica gel chromatography (98/2 hexane/EtOAc) provided 0.25 g of (4R)-4,8-dimethyl nonanoic acid t-butyl ester.

(4R)-4,8-dimethyl nonanoic acid: (4R)-4,8-dimethyl nonanoic acid t-butyl ester in 25 mL $CH_2Cl_2$ at 0° C. was treated with TFA (6 mL). The mixture was allowed to reach ambient temperature and stir overnight. The solvent was removed by rotary evaporation, and the mixture was purified by silica gel chromatography (95/5 hexane/EtOAc) to give 0.962 g (4R)-4,8-dimethyl nonanoic acid. m/z 185 (M−).

3-(4R,8-Dimethyl-nonanoyl)-4(S)-methyl-5(R)-phenyl-oxazolidin-2-one: A procedure similar to (4R,5S)-4-Methyl-3-(R)-4-methyl-heptanoyl)-5-oxazolidin-2-one was utilized to give 3-(4R,8-Dimethyl-nonanoyl)-4(S)-methyl-5(R)-phenyl-oxazolidin-2-one (1.35 g) m/z 346.5 (M+).

[4R,8-Dimethyl-2R-(4R-methyl-2-oxo-5R-phenyl-oxazolidine-3-carbonyl)-nonyl]-carbamic acid benzyl ester: To a solution of 3-(4(R),8-Dimethyl-nonanoyl)-4(S)-methyl-5 (R)-phenyl-oxazolidin-2-one (1.05 g, 3.04 mmol) in $CH_2Cl_2$ (12 mL) and $TiCl_4$ (3.04 mL of a 1 M solution in $CH_2Cl_2$) was added diisopropyl ethyl amine (0.55 mL, 3.19 mmol) at −20° C. The resulting dark red solution was stirred at −20° C. for 30 min prior to the addition of a solution of N-methoxymethyl benzyl carbamate (0.652 g, 3.34 mmol) in $CH_2Cl_2$ (3.5 mL) and $TiCl_4$ (3.34 mL). The mixture was stirred at 0° C. for 4 h. The reaction was quenched by the addition of saturated aqueous ammonium chloride solution. The mixture was extracted with $CH_2Cl_2$ (3×5 mL). The organics were combined and washed with 1 N HCl and neutralized with NaOH, followed by washing with brine. The organics were dried ($MgSO_4$), filtered, concentrated and purified by silica gel chromatography (95/5 hexane /EtOAc) to give 0.555 g [4R,8-Dimethyl-2R-(4R-methyl-2-oxo-5R-phenyl-oxazolidine-3-carbonyl)-nonyl]-carbamic acid benzyl ester.

2(R)-(Benzyloxycarbonylamino-methyl)-4(R),8-dimethyl-nonanoic acid: A procedure similar to that of (S)-2-((R)-2-Methyl=pentyl)succinic acid t-butyl ester was utilized to provide 0.198 g 2(R)-(Benzyloxycarbonylamino-methyl)-4(R),8-dimethyl-nonanoic acid.

2-aminomethyl-4,8-dimethyl nonanoic acid: 2(R)-(Benzyloxycarbonylamino-methyl)-4(R),8-dimethyl-nonanoic acid (0.148 g, 0.566 mmol) was treated with hydrogen in the presence of 20% pd/C to give 0.082 g of 2-aminomethyl-4,8-dimethyl nonanoic acid after filtration and purification via silica gel chromatography (85/15 $CH_2Cl_2$/MeOH). m/z 216.3 (M+).

Example 10

2-Aminomethyl-4,4,8-trimethyl-nonanoic acid 2,2,6-Trimethyl-heptanoic acid methyl ester: To diisopropyl amine (1.54 mL, 11.03 mmol) in THF (22 mL) at −78° C. was added nBuLi (6.89 mL of a 1.6 M solution in hexane). The solution was stirred for 30 min at −78° C., followed by the addition of methyl isobutyrate (0.97 mL, 8.48 mmol). The mixture was stirred at −78° C. for 2 h, and then 1-iodo-4-methyl pentane (1.8 g, 8.48 mmol) and DMPU (0.55 mL, 4.24 mmol) in THF (6 mL) was added. The reaction was stirred at −78° C. and allowed to slowly reach ambient temperature over 16 h. The reaction was quenched by the addition of ammonium chloride (saturated aqueous solution), and the mixture was extracted with EtOAc (2×10 mL). The organics were combined, washed with water, dried ($MgSO_4$), filtered and concentrated. Silica gel chromatography (99/1 hexane/EtOAc) provided 1.57 g of 2,2,6-Trimethyl-heptanoic acid methyl ester.

2,2,6-Trimethyl-heptan-1-ol: 2,2,6-Trimethyl-heptanoic acid methyl ester (1.97 g, 10.6 mmol) was taken up in toluene (65 mL) and cooled to −78° C. DiBALH (12.7 mL of a 1 N solution in toluene) was added dropwise. After 45 min, 1.5 mL DiBALH was added. After 2 h, the reaction was quenched by the addition of 15 mL MeOH at −78° C. The mixture was warmed to ambient temperature, and then cooled again to −78° C. for the addition of 10 mL 1 N HCl. The mixture was extracted with EtOAc (3×15 mL). The combined organics were washed with brine, dried ($MgSO_4$), filtered and concentrated. The residual oil was purified via silica gel chromatography (95/5 Hexane/EtOAc) to give 2,2,6-Trimethyl-heptan-1-ol (0.88 g). m/z 159 (M+).

2,2,6-Trimethyl-heptanal: Pyridinium chlorochromate (PCC, 4.17 g, 19.4 mmol) was combined with neutral alumina (14.6 g) in $CH_2Cl_2$ and stirred at ambient temperature for 15 min. The alcohol was diluted in $CH_2Cl_2$, and the mixture was stirred at ambient temperature for 2 h. The solution was filtered through a pad of silica, and the solids were washed with $CH_2Cl_2$. The filtrate was evaporated to give1.05 g m/z 157 (M+).2,2,6-Trimethyl-heptanal which was carried on without further purification.

2-Cyano-4,4,8-trimethyl-non-2-enoic acid benzyl ester: To a mixture of 2,2,6-Trimethyl-heptanal (1.05 g, 6.73 mmol), piperidine (0.19 mL, 2.01 mmol) and benzyl cyanoacetate (1.29 g, 7.4 mmol) in toluene (50 mL) was added glacial acetic acid (0.72 g, 12.1 mmol). The flask was fitted with a Dean-Stark trap, and the mixture was heated at reflux for 18. The mixture was cooled, treated with dilute HCl, and the layers were separated. The organics were washed with a saturated sodium bicarbonate solution followed by brine, and dried ($MgSO_4$), filtered and concentrated. The residual oil was purified by silica gel chromatography (98/2 hexane/EtOAc) to give 1.3 g of 2-Cyano-4,4,8-trimethyl-non-2-enoic acid benzyl ester m/z 314 (M+).

2-aminomethyl-4,4,8-trimethyl-nonanoic acid: 2-Cyano-4,4,8-trimethyl-non-2-enoic acid benzyl ester (1.3 g, 4.14 mmol) in THF (50 mL) was treated with hydrogen in the presence of 20% Pd/C to give a mixture of the cyano acid and the cyano methyl ester. The mixture was purified by silica gel chromatography to give 278 mg of 80105×41-1-2. The acid was then treated with hydrogen in the presence of Raney Ni in MeOH/NH4OH to give 0.16 g of 2-aminomethyl-4,4,8-trimethyl-nonanoic acid. m/z 230.3 (M+).

Example 11

2-Aminomethyl-4-ethyl-octanoic acid

A procedure similar to that of 2-Aminomethyl-4,4,8-trimethyl-nonanoic acid was utilized to prepare 2-Aminomethyl-4-ethyl-octanoic acid from 2-ethylhexanal. m/z 202.1 (M+).

Example 12

2-Aminomethyl-4-ethyl-8-methyl-nonanoic acid

A procedure similar to that of 2-Aminomethyl-4,4,8-trimethyl-nonanoic acid was utilized to prepare 2-Aminomethyl-8-methyl-nonanoic acid from 2,6-di-t-butyl-4-methylphenyl cyclopropylcarboxylate. m/z 230.2 (M+).

Example 13

3-Amino-2-[1-(4-methyl-pentyl)-cyclopropylmethyl]-propionic acid.

A procedure similar to that of 2-Aminomethyl-4,4,8-trimethyl-nonanoic acid was utilized to prepare 2-Aminomethyl-8-methyl-nonanoic acid from 2,6-di-t-butyl-4-methylphenyl cyclopropylcarboxylate. m/z 228.2 (M+).

Example 14

2-Aminomethyl-4-ethyl-hexanoic acid

A procedure similar to 2-aminomethyl-4,8-dimethyl-nonanoic acid was used to prepare 2-aminomethyl-4-ethyl-hexanoic acid from 4-ethyl hexanoic acid. m/z 174.1.

Example 15

3(S)-Amino-3,5-dimethyl-heptanoic acid

2-Methyl-propane-2(S)-sulfinic acid (1,3-dimethyl-pentylidene)-amide: A solution of (S)-(−)-2-methyl-2-propane-sulfonamide (500 mg, 4.1 mmol), 4-methyl-2-hexanone (470 mg, 4.1 mmol), and Titanium(IV) ethoxide (1.7 mL, 8.3 mmol) was heated at reflux for 18 h. The reaction mixture was poured into 20 mL brine with rapid stirring. The resulting solution was filtered through celite, and the organic layer was separated. The aqueous layer was extracted with ethyl acetate (2×20 mL). The combined organics were dried ($Na_2SO_4$), filtered, and concentrated. The resultant oil was purified by silica gel chromatography (25% EtOAc in hexane) to give 575 mg of 2-Methyl-propane-2(S)-sulfinic acid (1,3-dimethyl-pentylidene)-amide as a yellow oil.

3,5-Dimethyl-3-(2-methyl-propane-2(S)-sulfinylamino)-heptanoic acid methyl ester: To a −78° C. solution of lithium bis(trimethylsilyl)amide (5.1 ml of a 1 M solution in THF) in THF (6 mL) was added methyl acetate ((0.41 mL, 5.1 mmol) dropwise. After stirring for 20 min, a solution of chlorotitanium triisopropoxide (2.5 ml, 10 mmol) in THF (3 mL) was added dropwise. After 1 hour, 2-Methyl-propane-2(S)-sulfinic acid (1,3-dimethyl-pentylidene)-amide (560 mg, 2.6 mmol) in THF (3 mL) was added dropwise at −78° C. The reaction was stirred at −78° C. for 5 h, and then quenched by the addition of 10 mL ammonium chloride solution and warmed to room temperature. The mixture was diluted with 10 mL water, and filtered. The aqueous layer was extracted with ethyl acetate (2×20 mL). The combined organics were washed with brine, dried ($Na_2SO_4$), filtered, and concentrated. The resultant oil was purified by silica gel chromatography (30% EtOAc in hexane) to give 360 mg of 3,5-Dimethyl-3-(2-methyl-propane-2(S)-sulfinylamino)-heptanoic acid methyl ester.

3(S)-Amino-3,5-dimethyl-heptanoic acid: 3,5-Dimethyl-3-(2-methyl-propane-2(S)-sulfinylamino)-heptanoic acid methyl ester (360 mg, 1.2 mmol) was dissolved in 6 N HCl (2 mL) and dioxane (2 mL) and heated at 100 C for 6 h. The mixture was cooled to room temperature, diluted with water, and extracted with EtOAc (15 mL). The organics were purified by ion exchange chromatography to give 3(S)-Amino-3,5-dimethyl-heptanoic acid (270 mg) and then repurification by silica gel chromatography (70:25:5 $CH_2Cl_2$/MeOH/$NH_4OH$) to give 203 mg of 3(S)-Amino-3,5-dimethyl-heptanoic acid as a white solid. m/z 174 ($C_9H_{19}NO_2$+H).

Example 16

3(S)-Amino-3,5-dimethyl-nonanoic acid

A procedure similar to that of 3(S)-Amino-3,5-dimethyl-heptanoic acid was used to prepare 3(S)-Amino-3,5-dimethyl-nonanoic acid. m/z 202.1 ($C_{11}H_{23}NO_2$+H).

Pharmaceutical Composition Examples

In the following Examples, the term 'active compound' or 'active ingredient' refers to a suitable combination or individual element of an alpha-2-delta ligand and a PDEV inhibitor and/or a pharmaceutically acceptable salt or solvate, according to the present invention.

(i) Tablet Compositions

The following compositions A and B can be prepared by wet granulation of ingredients (a) to (c) and (a) to (d) with a solution of povidone, followed by addition of the magnesium stearate and compression.

| Composition A | mg/tablet | mg/tablet |
|---|---|---|
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
|  | 500 | 300 |
| Composition B | mg/tablet | mg/tablet |
| (a) Active ingredient | 250 | 250 |
| (b) Lactose | 150 | 150 |
| (c) Avicel PH 101 | 60 | 26 |
| (d) Sodium Starch Glycollate | 20 | 12 |

-continued

| | | |
|---|---:|---:|
| (e) Povidone B.P. | 15 | 9 |
| (f) Magnesium Stearate | 5 | 3 |
| | 500 | 300 |

| Composition C | mg/tablet |
|---|---:|
| Active ingredient | 100 |
| Lactose | 200 |
| Starch | 50 |
| Povidone | 5 |
| Magnesium Stearate | 4 |
| | 359 |

The following compositions D and E can be prepared by direct compression of the admixed ingredients. The lactose used in formulation E is of the direct compression type.

| | mg/tablet |
|---|---:|
| Composition D | |
| Active ingredient | 250 |
| Magnesium Stearate | 4 |
| Pregelatinised Starch NF15 | 146 |
| | 400 |
| Composition E | |
| Active ingredient | 250 |
| Magnesium Stearate | 5 |
| Lactose | 145 |
| Avicel | 100 |
| | 500 |
| Composition F (Controlled release composition) | |
| (a) Active ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 700 |

The composition can be prepared by wet granulation of ingredients (a) to (c) with a solution of povidone, followed by addition of the magnesium stearate and compression.

Composition G (Enteric-Coated Tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-Coated Controlled Release Tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule Compositions

Composition A

Capsules can be prepared by admixing the ingredients of Composition D above and filling two-part hard gelatin capsules with the resulting mixture. Composition B (infra) may be prepared in a similar manner.

| | mg/capsule |
|---|---:|
| Composition B | |
| (a) Active ingredient | 250 |
| (b) Lactose B.P. | 143 |
| (c) Sodium Starch Glycollate | 25 |
| (d) Magnesium Stearate | 2 |
| | 420 |
| Composition C | |
| (a) Active ingredient | 250 |
| (b) Macrogol 4000 BP | 350 |
| | 600 |

Capsules can be prepared by melting the Macrogol 4000 BP, dispersing the active ingredient in the melt and filling two-part hard gelatin capsules therewith.

| Composition D | mg/capsule |
|---|---:|
| Active ingredient | 250 |
| Lecithin | 100 |
| Arachis Oil | 100 |
| | 450 |

Capsules can be prepared by dispersing the active ingredient in the lecithin and arachis oil and filling soft, elastic gelatin capsules with the dispersion.

| Composition E (Controlled release capsule) | mg/capsule |
|---|---:|
| (a) Active ingredient | 250 |
| (b) Microcrystalline Cellulose | 125 |
| (c) Lactose BP | 125 |
| (d) Ethyl Cellulose | 13 |
| | 513 |

The controlled release capsule formulation can be prepared by extruding mixed ingredients (a) to (c) using an extruder, then spheronising and drying the extrudate. The dried pellets are coated with a release controlling membrane (d) and filled into two-part, hard gelatin capsules.

| Composition F (Enteric capsule) | mg/capsule |
|---|---:|
| (a) Active ingredient | 250 |
| (b) Microcrystalline Cellulose | 125 |
| (c) Lactose BP | 125 |

| Composition F (Enteric capsule) | mg/capsule |
|---|---|
| (d) Cellulose Acetate Phthalate | 50 |
| (e) Diethyl Phthalat | 5 |
| | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-Coated Controlled Release Capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) or a plasticizer to prevent membrane cracking during application or on storage. Suitable plasticizers include diethyl phthalate, tributyl citrate and triacetin.

| (iii) Intravenous injection composition | |
|---|---|
| Active ingredient | 0.200 g |
| Sterile, pyrogen-free phosphate buffer (pH 9.0) to | 10 ml |

The active ingredient is dissolved in most of the phosphate buffer at 35-40° C., then made up to volume and filtered through a sterile micropore filter into sterile 10 ml glass vials (Type 1) which are sealed with sterile closures and overseals.

| (iv) Intramuscular injection composition | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (v) Syrup composition | |
|---|---|
| Active ingredient | 0.25 g |
| Sorbitol Solution | 1.50 g |
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| (vi) Suppository composition | |
|---|---|
| | mg/suppository |
| Active ingredient | 250 |
| Hard Fat, BP (Witepsol H15 - Dynamit NoBel) | 1770 |
| | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38-40° C., 2.02 g aliquots of the mixture are filled into suitable plastic moulds and the suppositories allowed to cool to room temperature.

| (vii) Pessary composition | |
|---|---|
| | mg/pessary |
| Active ingredient (63 lm) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

| (viii) Transdermal composition | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with a surface area of 10 cm$^2$.

The invention claimed is:

1. A combination consisting essentially of an alpha-2-delta ligand selected from gabapentin, pregabalin or a pharmaceutically acceptable salt or solvate thereof; and a PDEV inhibitor selected from: 5-[2-ethoxy-5-(4-methyl-1-piperazinylsulphonyl)phenyl]-I-methyl-3-n-propyl-1,6-dihydro-7H-pyrazolo[4,3-d]pyrimidin-7-one (sildenafil) or a pharmaceutically acceptable salt or solvate thereof; the alpha-2 delta ligand and the PDEV inhibitor being present in a ratio from 1:1 to 10:1 by weight.

2. A combination according to claim 1 wherein the alpha-2-delta ligand is gabapentin, or a pharmaceutically acceptable salt or solvate thereof.

3. A combination according to claim 1, wherein the alpha-2-delta ligand is gabapentin, or a pharmaceutically acceptable salt or solvate thereof.

4. A method of treating pain, the method comprising administering to a subject in need thereof a therapeutically effective amount of a combination consisting essentially of an alpha-2-delta ligand selected from gabapentin, pregabalin or a pharmaceutically acceptable salt or solvate thereof; and a PDEV inhibitor selected from: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil); or a pharmaceutically acceptable salt or solvate thereof; the alpha-2 delta ligand and the PDEV inhibitor being present in a ratio from 1:10 to 20:1 1:1 to 10:1 by weight.

5. A method according to claim 4, wherein the alpha-2-delta ligand is gabapentin, or a pharmaceutically acceptable salt or solvate thereof.

6. A method according to claim 4 wherein the alpha-2-delta ligand is pregabalin, or a pharmaceutically acceptable salt or solvate thereof.

* * * * *